(12) United States Patent
Park

(10) Patent No.: US 11,419,523 B2
(45) Date of Patent: *Aug. 23, 2022

(54) BLOOD VESSEL SIZING DEVICE AND METHOD FOR SIZING BLOOD VESSEL

(71) Applicant: SIZER LLC, St. Charles, IL (US)

(72) Inventor: Richard B. Park, St. Charles, IL (US)

(73) Assignee: SIZER LLC, St. Charles, IL (US)

( * ) Notice: Subject to any disclaimer, the term of this patent is extended or adjusted under 35 U.S.C. 154(b) by 529 days.

This patent is subject to a terminal disclaimer.

(21) Appl. No.: 16/412,758

(22) Filed: May 15, 2019

(65) Prior Publication Data

US 2019/0261894 A1 Aug. 29, 2019

Related U.S. Application Data

(63) Continuation of application No. 15/192,318, filed on Jun. 24, 2016, now Pat. No. 10,314,519, which is a
(Continued)

(51) Int. Cl.
*A61B 5/107* (2006.01)
*A61B 6/00* (2006.01)
(Continued)

(52) U.S. Cl.
CPC ........ *A61B 5/1075* (2013.01); *A61B 5/02007* (2013.01); *A61B 5/1079* (2013.01);
(Continued)

(58) Field of Classification Search
CPC . A61B 5/1075; A61B 5/02007; A61B 5/1079; A61B 6/504; A61B 6/5217;
(Continued)

(56) References Cited

U.S. PATENT DOCUMENTS 3,812,842 A 5/1974 Rodriguez
4,061,924 A 12/1977 Jacoby et al.
(Continued)

FOREIGN PATENT DOCUMENTS

CN 203436327 U 2/2014
JP 2012081136 A 4/2012
WO 2010064049 A1 6/2010

OTHER PUBLICATIONS

International Search Report and Written Opinion, issued in connection with international application serial No. PCT/US2013/033154, dated Jun. 14, 2013, 9 pages.
(Continued)

*Primary Examiner* — Sanjay Cattungal
(74) *Attorney, Agent, or Firm* — Banner & Witcoff, Ltd.

(57) ABSTRACT

Medical devices and methods for determining the size of blood vessels are disclosed. In one implementation, a blood vessel sizing device is configured for placement on an area of skin of a patient. The device includes a plurality of radiopaque concentric-circle elements. In one implementation, a blood vessel sizing method includes placing a marker having a plurality of concentric-circle elements on the skin of a patient, imaging a blood vessel of the patient and the device, and comparing the imaged blood vessel to the imaged circles to determine the blood vessel size, the concentric-circle elements allowing a determination of size without errors of parallax.

20 Claims, 16 Drawing Sheets

Related U.S. Application Data continuation of application No. 14/248,101, filed on Apr. 8, 2014, now Pat. No. 9,375,167, which is a continuation-in-part of application No. 13/427,084, filed on Mar. 22, 2012, now Pat. No. 8,971,995.

(51) Int. Cl.
*A61B 5/02* (2006.01)
*A61B 90/00* (2016.01)
*A61B 17/00* (2006.01)

(52) U.S. Cl.
CPC ............ *A61B 6/504* (2013.01); *A61B 6/5217* (2013.01); *A61B 90/39* (2016.02); *A61B 2017/00907* (2013.01); *A61B 2090/3966* (2016.02); *A61B 2090/3991* (2016.02); *A61B 2560/0412* (2013.01)

(58) Field of Classification Search
CPC .......... A61B 90/39; A61B 2017/00907; A61B 2090/3966; A61B 2090/3991; A61B 2560/0412
See application file for complete search history.

(56) References Cited

U.S. PATENT DOCUMENTS

| | | |
|---|---|---|
| 4,506,676 A | 3/1985 | Duska |
| 5,150,292 A | 9/1992 | Hoffmann et al. |
| 5,193,106 A | 3/1993 | DeSena |
| 5,216,700 A | 6/1993 | Cherian |
| 5,400,513 A | 3/1995 | Duffield |
| 5,970,119 A | 10/1999 | Hofmann |
| 6,084,941 A | 7/2000 | Stenstrom |
| 6,333,970 B1 | 12/2001 | LeMaitre et al. |
| 6,356,621 B1 | 3/2002 | Furumori et al. |
| 6,733,489 B2 | 5/2004 | Nutting et al. |
| 7,127,826 B2 | 10/2006 | Russell |
| 7,602,883 B2 | 10/2009 | Joseph et al. |
| 7,860,290 B2 | 12/2010 | Gulsun et al. |
| 7,876,884 B2 | 1/2011 | Davis |
| 7,978,825 B2 | 7/2011 | Ngo |
| 8,057,396 B2 | 11/2011 | Forster et al. |
| 8,298,147 B2 | 10/2012 | Huennekens et al. |
| 8,340,781 B2 | 12/2012 | Konishi |
| 8,611,697 B2 | 12/2013 | Nathaniel et al. |
| 8,655,042 B2 | 2/2014 | Florent |
| 2004/0034298 A1 | 2/2004 | Johnson et al. |
| 2004/0086082 A1 | 5/2004 | Foos et al. |
| 2004/0133129 A1 | 7/2004 | Harari et al. |
| 2005/0000133 A1* | 1/2005 | Russell ................. A61B 90/39 40/630 |
| 2007/0163139 A1* | 7/2007 | Russell ................. A61B 90/39 33/758 |
| 2007/0213686 A1 | 9/2007 | Mathur et al. |
| 2007/0280406 A1 | 12/2007 | Geliebter |
| 2008/0187245 A1 | 8/2008 | Habets et al. |
| 2009/0022272 A1 | 1/2009 | Joseph et al. |
| 2009/0253981 A1 | 10/2009 | Hamilton et al. |
| 2012/0059244 A1 | 3/2012 | McClelland et al. |
| 2012/0302863 A1* | 11/2012 | O'Neill ................. A61B 90/39 600/407 |
| 2013/0253301 A1 | 9/2013 | Park |
| 2014/0064582 A1 | 3/2014 | Schmidt et al. |
| 2014/0221874 A1 | 8/2014 | Park |
| 2017/0309016 A1 | 10/2017 | Klaiman et al. |

OTHER PUBLICATIONS

Feb. 4, 2016—(WO) Invitation to Pay Additional Fees and Partial Search Report—App. No. PCT/US2015/024925—6 pages.
Apr. 19, 2016—(WO) International Serch Report and Written Opinion—App. No. PCT/US2015/024925—17 pages.
Jan. 23, 2018—(WO) International Search Report and Written Opinion—App. No. PCT/US2017/055606—16 pages.
Sep. 18, 2019—(CN) Office Action—App. No. 201580030664.5.

* cited by examiner

BLOOD VESSEL SIZING DEVICE AND METHOD FOR SIZING BLOOD VESSEL

CROSS REFERENCE TO RELATED APPLICATION

This application is a continuation of U.S. patent application Ser. No. 15/192,318 filed Jun. 24, 2016, which is a continuation of U.S. patent application Ser. No. 14/248,101, filed Apr. 8, 2014, now U.S. Pat. No. 9,375,167, which is a continuation-in-part of U.S. patent application Ser. No. 13/427,084, which was filed on Mar. 22, 2012, now U.S. Pat. No. 8,971,995, the disclosures of which are hereby incorporated by reference in their entireties for any and all non-limiting purposes.

BACKGROUND

The present disclosure relates generally to medical devices and more specifically to systems and methods for determining dimensions of imaged objects on a graphical representation medical devices for determining or measuring blood vessel size during, for example, an angiogram.

Determining blood vessel size quickly and accurately is important, for example, when treating stenotic vessels with angioplasty or stent. If blood vessel size is incorrectly determined, a stent that is too large for the actual blood vessel size could be selected. Using an oversized stent can damage, dissect or even perforate the passageway it is included to be filled within.

Diagnostic imaging using, for example, X-ray machines, computer tomography machines or magnetic resonance imaging machines, generate images of blood vessels including any narrowing of blood vessels. A clinician uses these images to determine blood vessel size and stenosis. But using such images has inherent limitations. For example, computer tomography imaging accuracy can be affected by sampling, size of display field of view and/or intravascular density of a contrast material. During emergency procedures, computer tomography or magnetic resonance imaging measurements may not be available.

A need accordingly exists for medical devices and methods that improve the process of determining blood vessel size during, for example, angiographic procedures.

SUMMARY

Aspects of the present disclosure relate to systems, devices, and methods that provide a more accurate dimension (e.g., a length) of a feature represented in a graphical representation of an imaged object (e.g., an imaged body portion represented in a radiograph captured by a radiograph process. In one example, the present disclosure is directed to medical devices and methods that more accurately provide the measurements of imaging targets. In one implementation, the devices and methods described herein may be configured to determine blood vessel sizes with greater accuracy, based upon, for example, angiographic images of the vessels. Such blood vessel images can be generated, for example, via angiograms. In one implementation, a blood vessel sizing device is configured for placement on the skin of a patient near an imaging target (e.g. a blood vessel to be imaged). Accordingly, the device may include a plurality of radiopaque concentric-circle elements of known size. When a computer machine generates an angiographic image of the blood vessel, the radiopaque concentric-circle elements cause the circles to be visible on the generated image (along with the blood vessel image). As such, a clinician may quickly and accurately determine the actual size (true dimension/length) of the blood vessel by comparing the blood vessel image to the image of the concentric circles, which have a known or illustrated dimension.

In one aspect, the systems and methods described herein include a blood vessel sizing device having a rigid planar base structure with a front surface and a back surface. The blood vessel sizing device further has a plurality of radiopaque concentric-circle elements and a plurality of radiopaque symbols positioned on the front surface of the base structure. Additionally, the device has a deformable structure attached to the back surface of the base structure, and an adhesive layer attached to a back surface of the deformable structure.

In another aspect, a blood vessel sizing device is described as having a rigid planar base structure with a plurality of radiopaque concentric-circle elements positioned on a front surface. Additionally, the front surface of the base structure has a plurality of radiopaque symbols representing dimensions of the concentric-circle elements.

In yet another aspect, a non-transitory computer-readable medium comprising computer-executable instructions is described for automated determination of a true dimension of a biological feature present in a radiological image. The instructions include receiving data corresponding to a biological feature in a radiological image, determining a length property of the biological feature, and identifying elements from image data last corresponds to radiopaque concentric-circle elements of known size. The instructions further include identifying dimensional properties for the identified elements, determining a longest axis of the identified concentric-circle elements, and comparing the length property of the biological feature to the concentric-circle elements along the longest axis. Subsequently, the determined length property may be converted into a true dimension value, and communicated to a user.

It is accordingly an advantage of the present disclosure to provide a medical device that simplifies and improves blood vessel size determination, and without errors of parallax It is a further advantage of the present disclosure to provide a method for improving the process for blood vessel size determination.

Additional features and advantages are described herein, and will be apparent from the following Detailed Description and the figures.

DETAILED DESCRIPTION

In one example, the present disclosure is directed to medical devices and methods that allow more accurate determinations of one or more dimensions (e.g., length, height, depth) of target objects targeted to be captured by an imaging technique. Such target objects may include biological features, e.g. living passageways (such as blood vessels), items within living passageways (e.g., blood clots), and/or any object that may be imaged with one or more imaging techniques. Yet, other embodiments may capture one or more objects in a target area that is targeted by an image technique. Using a medical example, a user may be experiencing pain in a general or specific area of their body. Therefore, it may be desired to utilize an imaging device to capture an image of the area without specifically targeting a specific object or feature. Thus, the device may be configured to capture a target area with one or more objects of interest.

The terms "graphical representation" and "image" are used herein to refer to an output of an imaging technique. Such imaging techniques that generate the graphical representations/images may include one or more processes (which may not be mutually exclusive, and may be combined with other processes, including non-image based processes), to provide an output comprising a graphical representation or image of a target area and/or target object, including an angiogram, MRI, X-Ray, CT scan, myelogram, thermograph, MRN, ultrasound, and/or combinations thereof or other mechanisms that can produce a graphical representation or image of a target object or target area. Further, those of ordinary skill in the art will readily appreciate that the systems and methods described herein may be utilized for non-biological purposes (e.g. for imaging of synthetic materials, and the like), and without departing from the disclosures herein.

Figure 1:
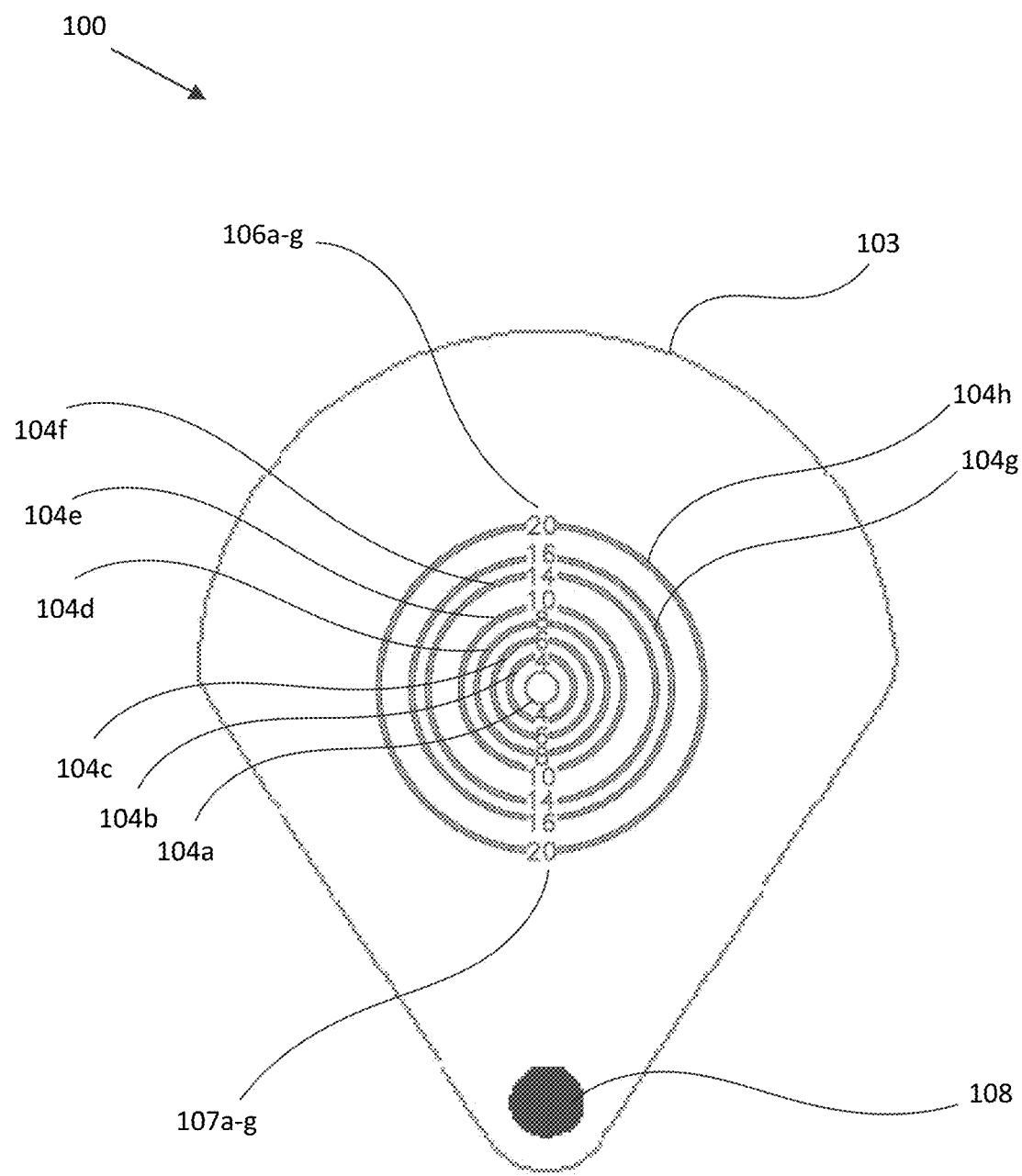
FIG. 1 is a plan view of a blood vessel sizing device.

FIG. 1 schematically depicts a device 100 configured for providing a mechanism to determine one or more dimensions of features in a graphical representation of an imaged object or area. In one implementation, device 100 may be configured to be placed in an area to be imaged, such as, contact with an area of skin of a patient prior to a medical imaging procedure, and such—device 100 may be utilized to determine a true dimension/length of one or more biological features to be imaged using an imaging technique (e.g. an angiogram using x-rays, and the like).

In particular, device 100 may comprise a base structure 102. Positioned on the base structure 102 or another surface are shown a plurality concentric-circle elements, numbered as elements 104a-104h, and a plurality symbols, numbered as symbols 106a-106g and 107a-107g. In one example, the elements 104a-104h, and symbols 106a-106g and 107a-107g, may comprise a radiopaque (radiodense) metal, a radiopaque alloy, or another radiopaque material known to those of ordinary skill in the art, and wherein radiopacity will be readily understood to those of ordinary skill in the art as a property of a material that substantially reduces and/or prevents electromagnetic radiation of a certain wavelength/range of wavelengths from passing through the material. In particular, radiopacity may be understood as a property of a material that substantially reduces and/or prevents x-rays from passing through the material. In yet other embodiments, materials that are reactive to certain imaging techniques or chemical processes may also be utilized. In this regard, the elements and symbols herein (including elements 104, symbols 106 and/or 107) may be configured to reduce or prevent transmission of wavelengths such as to appear opaque. In yet other embodiments, they may contain materials known to contrast with an intended target object or target area, such as would be similar to the use of contrast agents in radiological sciences. In yet another embodiment, at least one element and/or symbol may comprise a material that is configured to be fluoresce as a result of being imaged or some mechanism utilized prior to or during the imaging process(es).

In one example, one or more of elements 104a-104h and/or symbols 106a-106g may be provided directly, e.g., printed, onto base structure 102 using, e.g. any appropriate printing method known to those of ordinary skill in the art. In other examples, one or more of elements 104a-104h and/or symbols 106a-106g and 107a-107g may be molded into base structure 102, fastened to base structure 102 by any appropriate fastener, or adhered/welded to base structure 102, and the like.

In one example, base structure 102 may comprise one or more of a polymeric material, a glass, a metal, an alloy, or any other material with material properties that give rise to a contrast between base structure 102 and one or more of elements 104a-104h, symbols 106a-106g and 107a-107g, and/or location marker 108 when imaged using electronic radiation of a particular wavelength/range of wavelengths (e.g., x-rays). In one example, base structure 102 may comprise a polymer that is substantially transparent to electromagnetic radiation in the visible spectrum (e.g. visible light). As discussed above, certain elements (104) or symbols (106,107) may be configured to be opaque and/or react to different imaging processes.

In one implementation, base structure 102 may comprise a material with mechanical properties exhibiting a level of rigidity such that base structure 102 does not readily conform to one or more undulations of a surface onto which it is positioned. In one example, this rigidity may be achieved by selecting base structure 102 with a material thickness corresponding to an appropriate level of rigidity. Specifically, in one example, base structure 102 may comprise a polymeric material with a thickness of 0.25 mm, 0.5 mm, 0.75 mm, 0.9 mm, among many others.

In one implementation, concentric-circle elements 104a-104h may have known diameters. In one example, the diameters of the elements 104a-104h may measure 2 mm, 4 mm, 6 mm, 8 mm, 10 mm, 14 mm, 16 mm, 20 mm or 30 mm. However, as will be readily apparent to those of ordinary skill in the art, differently sized concentric-circle elements 104a-104h may be used without departing from the scope of this disclosure. Furthermore, a different number of elements than those eight elements represented as 104a-104h may be used on device 100 without departing from the scope of this disclosure. In one example, elements 104a-104h may have a thickness (line thickness) of approximately 0.25 mm, and wherein the diameter of each of the elements 104a-104h is measured to the center of the radiopaque line that makes up each of the elements 104a-104h. In one implementation, and as depicted in FIG. 1, one or more symbols (e.g., symbols 106a-106g and/or 107a-107g) may intersect one or more of the elements 104a-104g. In this way, a symbol may serve as an indicator of a dimensional property of a element with which it intersects. For example, a symbol may denote a radius or diameter of a concentric-circle elements with which it intersects. In another example, a symbol may not intersect with a element for which it denotes a dimensional property. In the specific example depicted FIG. 1, a plurality of symbols denote a plurality of diameters of respective concentric-circle elements. Specifically, symbols 106a and 107a are shown as being diametrically opposed on the concentric-circle element 104b, and indicate that concentric-circle element 104b has a diameter of 4 mm. Similarly, symbols 106b and 107b indicate that concentric-circle element 104c has a diameter of 6 mm; symbols 106c and 107c indicate that concentric-circle element 104d has a diameter of 8 mm; symbols 106d and 107d indicate that concentric-circle elements 104e has a diameter of 10 mm; symbols 106e and 107e indicate that concentric-circle element 104f has a diameter of 14 mm; symbols 106f and 107f indicate that concentric-circle element 104g has a diameter of 16 mm; and symbols 106g and 107g indicate that concentric-circle element 104h has a diameter of 20 mm. Yet in another embodiment, one or more elements may have a diameter of 30 mm.

In one example, and as depicted in FIG. 1, symbols 106a-106g are embodied as numerals (e.g. Arabic numerals). Those of ordinary skill in the art, however, will readily understand that any symbol may be used to denote a dimensional property (e.g., a diameter) of one or more of concentric-circle elements 104a-104h. for example, symbols 106a-106g may be computer-readable shapes and/or patterns (e.g. barcodes, and the like). Indeed, in certain embodiments, a symbol or marker may provide computer-readable indicia that may be detected (including automatically) before, during, or after an imaging process. In certain embodiments, the symbol or indicia may not readily convey the dimensional property represented without prior knowledge to its correlation to the dimensional property.

In one implementation, device 100 has a location marker 108, wherein location marker 108. Location marker, like the elements and symbols described herein, may comprise a radiopaque area, contrast materials, and/or fluorescent materials. In one implementation, location marker 108 has a surface area of between 18 and 22 mm². Location marker 108 may be distanced a predetermined distance from at least one or more of elements 104, symbols 106 and/or symbols 107. In one embodiment, the diameter of the a concentric circle, such as circle 104h, may be less than, equal to, or larger than the distance from location marker to that circle, the center of the concentric circles 104a, or another location associated with the circles 104 or symbols 106/107. In yet another embodiment, a dimension (e.g., diameter) of marker 108 may be proportional to one or more aspects of the circles 104, and/or symbols 106/107.

In one example, electromagnetic radiation of a certain wavelength (e.g. x-rays) may not pass through, and/or the transmission of the radiation may be substantially attenuated through elements 104a-104h, symbols 106a-106g and 107a-107g, and/or location marker 108. Accordingly, a radiological image (otherwise referred to as a radiograph, or x-ray, and the like) of a biological and/or synthetic feature may include a representation or image corresponding to one or more of elements 104a-104h, symbols 106a-106g and 107a-107g, and location marker 108.

In one implementation, location of one or more of elements 104a-104h, and/or symbols 106a-106g and 107a-107g may be aided by location marker 108, wherein location marker 108 has a comparatively larger radiopaque surface area than anyone element 104a-104h or symbol 106a-106g or 107a-107g. As such, the comparatively larger radiopaque surface area of location marker 108 may correspond to a larger feature within a radiological image produced using device 100. Accordingly, location marker 108 may be relatively more visible to a user, and hence, more quickly recognized in a produced radiological image. One or more of elements 104, symbols 106/107, and/or marker 108 may be configured to have a first appearance when imaged under a first imaging process and second appearance when imaged under a second image process. This may be beneficial for a few reasons. In one embodiment, it may allow the detection of whether the proper procedure was used, and/or what type of procedure was used. In one embodiment, the first appearance may be configured to present itself on a graphical representation when a first wavelength was used and the second appearance may be associated with a second wavelength, such as one that may be erroneously used for a specific instance.

FIG. 1 depicts device 100 having base structure 102 with an outer perimeter 103 having a discrete shape. Those of ordinary skill in the art will recognize that base structure 102 (and/or entire device 100) may have any shape, and without departing from the scope of this disclosure. In this way, one alternative implementation of device 200 is depicted in FIG. 2.

Figure 2:
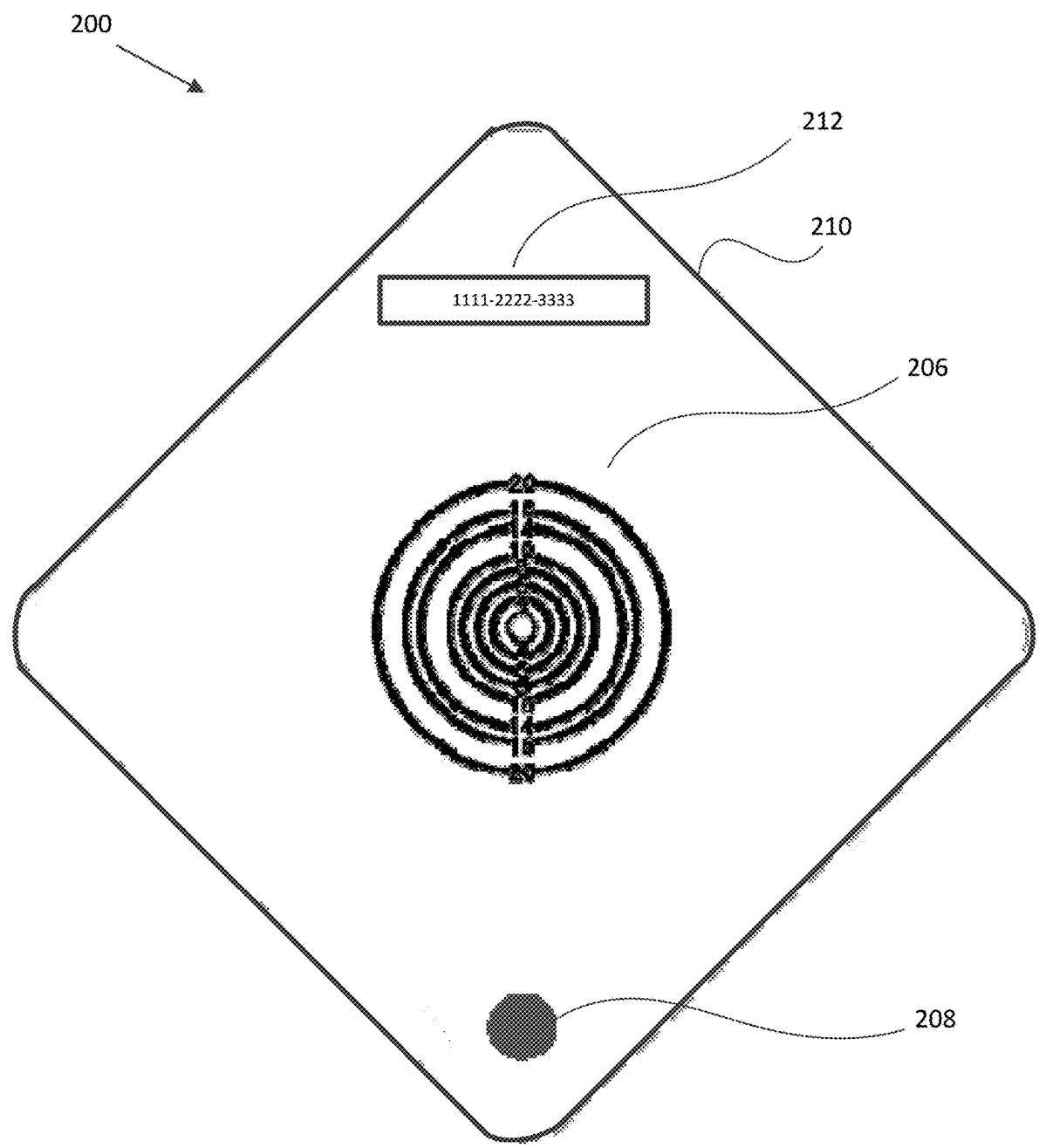
FIG. 2 is a plan view of an alternative implementation of a blood vessel sizing device.

FIG. 2 depicts device 200, which may be similar in one or more aspects to device 100 from FIG. 1. In particular, device 200 has a base structure 202 that may be similar in structural features to base structure 102 from FIG. 1. In this example, base structure 202 is embodied with outer perimeter 210, which exhibits a different shape than outer perimeter 103 of device 100. Device 200 further includes a scale 206 located thereon. In one example, scale 206 may comprise one or more elements like or similar to elements 104a-104h and/or symbols 106a-106g and 107a-107g from FIG. 1, including in relation to one or more of their quantity, size, shape, proportional dimensions, radio opacity, and combinations thereof. Further, location marker 208 may be similar (in terms of dimension, location, and/or other attributes, such as those described above) to location marker 108 from FIG. 1.

One or more devices, such as devices 100 or 200, may include a unique identifier. In one example, device 200 comprises a unique identifier 212. Unique identifier 212 may be provided, e.g., printed, onto base structure 202. In one specific example, unique identifier 212 may comprise a radiopaque material. In one example, unique identifier 212 may be used to associate one or more data points with device 200. For example, unique identifier 212 may be used to identify a patient imaged using device 200 (e.g. to produce, in one example, an x-ray), the specific imaging equipment, personnel employing the imaging technique, date, time, locational information, and combinations thereof, among others. Those of ordinary skill in the art will readily understand that unique identifier 212 may be utilized to associate a device, such as device 100 or device 200, with any type of stored information, wherein the unique identifier 212 itself may store said information, or wherein unique identifier 212 may comprise a sequence of digits and/or symbols that may be used to look up information stored in a collection of information, whether electronic or not, separate from the device 100/200.

Figure 3A:
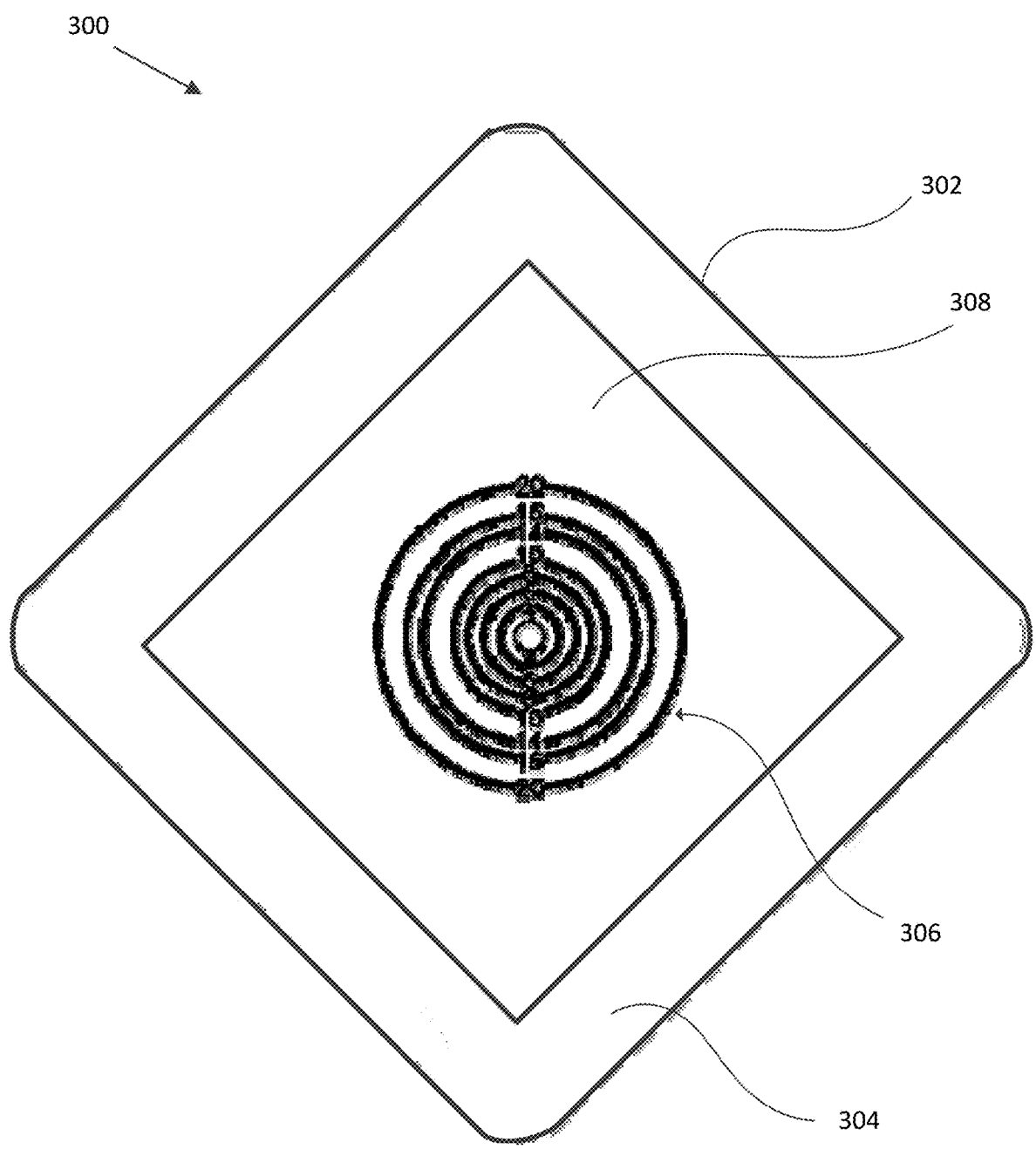
FIG. 3A-3B depicts alternative implementations of blood vessel sizing devices.

FIG. 3A depicts a blood vessel sizing device 300 which may be similar in one or more aspects to one or more of devices 100 and/or 200 from FIG. 1 and FIG. 2, respectively. Device 300 is shown as comprising a base structure 302, wherein, in one example, base structure 302 may be similar to base structure 102 and/or 202 from FIG. 1 and FIG. 2, respectively. Furthermore, device 300 has a scale 306, which may be similar to scale 206 from FIG. 2.

In the example depicted in FIG. 3A, base structure 302 comprises a substantially transparent (e.g. to light in the visible spectrum) polymeric material. Accordingly, this transparency may be utilized when positioning device 300 on an area of skin of a patient and/or other surface (biological or synthetic) prior to an imaging procedure (e.g. an x-ray).

In one example, device 300 may comprise a perimeter area 304, wherein perimeter area 304 may represent an area of the base structure 302 to which one or more of an adhesive layer or a deformable structure (described further in relation to FIG. 4 and FIG. 5) may be affixed. In one example, that adhesive layer and/or deformable structure (not pictured) affixed to perimeter area 304 may be opaque to light in the visible spectrum and/or spectrum of wavelengths utilized by an imaging process. In one implementation in which the perimeter area 304 is opaque to light in the visible spectrum, perimeter area 304 encloses a window 308 of base structure 302, wherein that area of base structure 302 designated as window 308 remains substantially transparent to light in the visible spectrum. As such, window 308 facilitates visual positioning of device 300 on an area of interest prior to an imaging procedure while perimeter area 304 is substantially opaque. In certain embodiments, the perimeter area may be opaque with respect to only one of (a) light in the visible spectrum and (b) spectrum of wavelengths utilized by an imaging process to capture the target object or target area.

It will be readily apparent to those of skill in the art that while perimeter area 304 is depicted in FIG. 3A with a particular shape, many alternative shapes for perimeter area and/or window 308 may be realized without departing from the scope of this disclosure. Furthermore, in another example, perimeter area 304 may cover substantially the same area as base structure 302, and without departing from the scope of this disclosure.

Figure 3B:
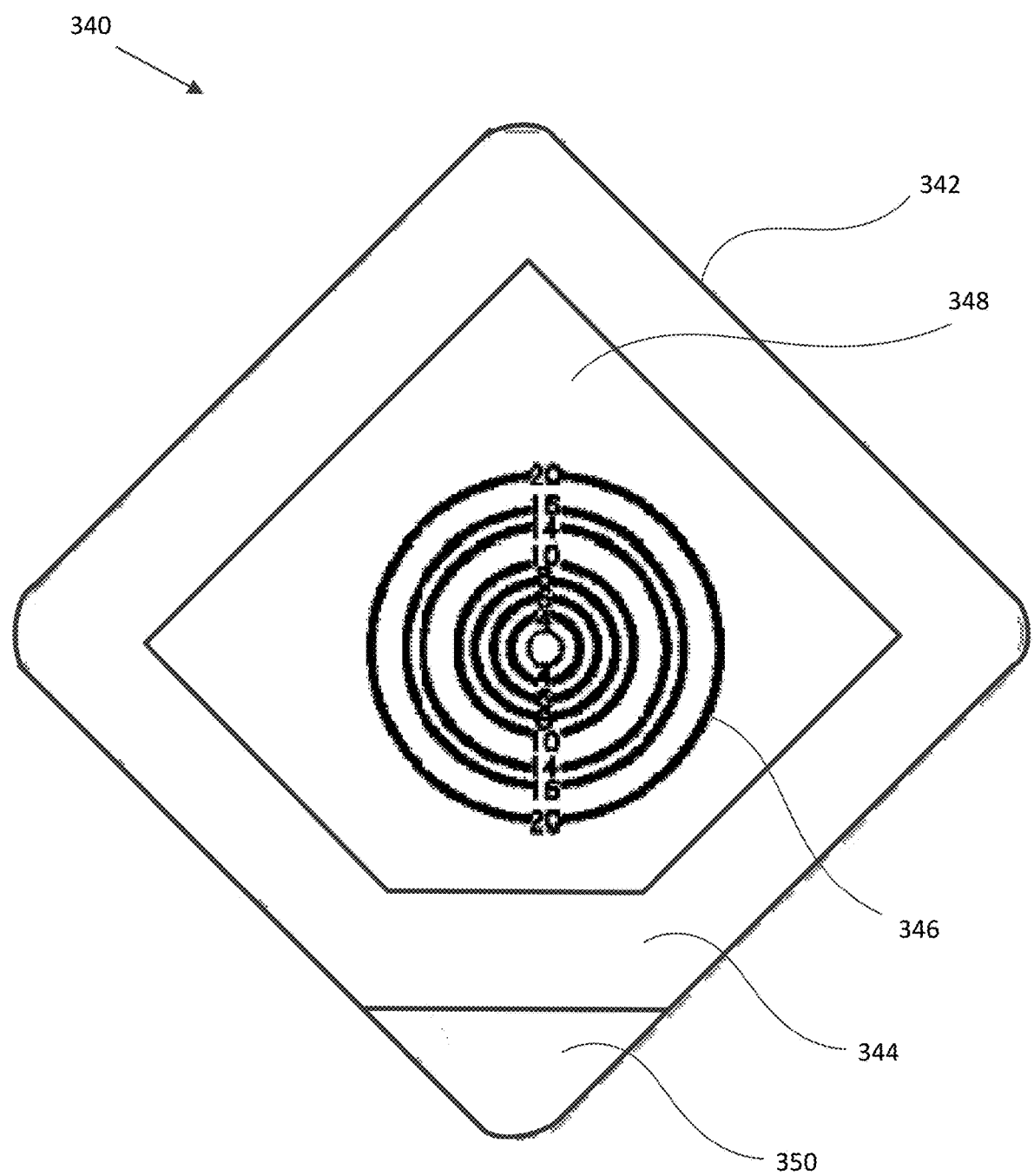

FIG. 3B depicts a device 340, wherein device 340 may be similar to device 300 from FIG. 3A. Similarly to device 300, device 340 may have a substantially transparent base structure 342. Furthermore, base structure 342 may have a perimeter area 344, wherein perimeter area 344 represents an area to which one or more of an adhesive layer and/or a deformable structure may be affixed. Accordingly, perimeter area 344 may be substantially opaque to light in the visible spectrum. As such, visual placement of device 340 on an area of interest may be facilitated by a substantially transparent window 348. It is noted that window 348, and similarly for window 308, while being substantially transparent to light in the visible spectrum, include radiopaque scales 346 and 306, wherein scales 346 and 306 may be substantially opaque to light in the visible and/or x-ray spectrum, among others.

Figure 4A:
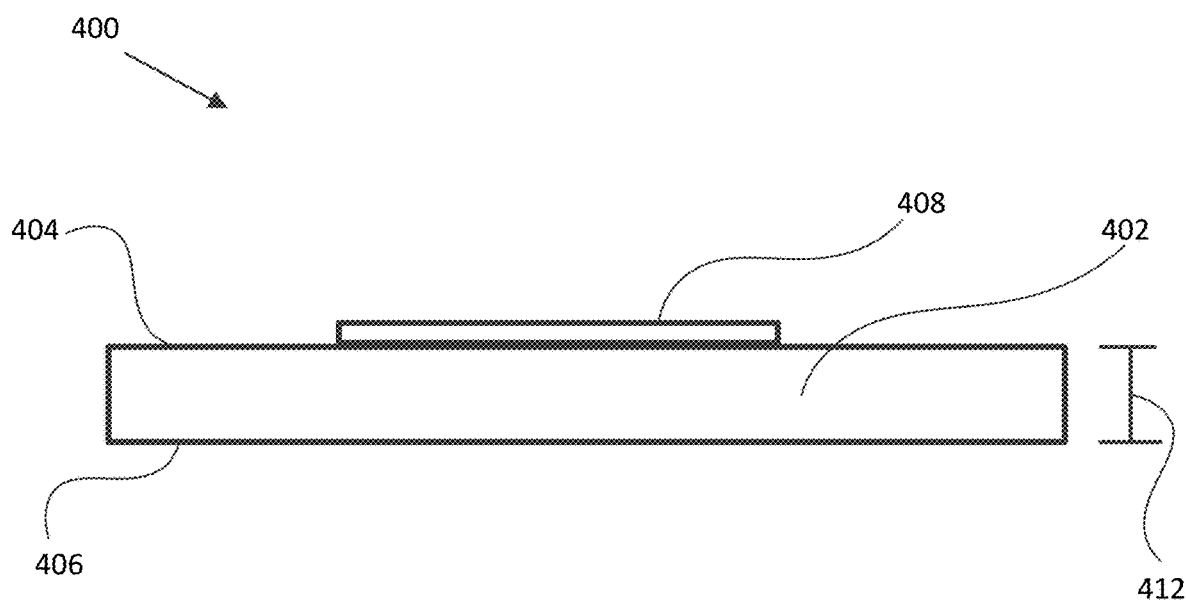
FIG. 4A-4B schematically depict side views of blood vessel sizing devices.

In one example implementation, device 340 comprises a tab structure 350, wherein tab structure 350 may be an area of base structure 342 that is non-adhesive. As such, structure 350 may facilitate removal of device 340 from an area to which device 304 he was adhered prior to an imaging procedure. An adhesive layer may be positioned on the entirety of or just a portion of the FIG. 4A schematically depicts a side view of an imaging device 400, similar to devices 100, 200, and/or 300 (wherein FIG. 1, FIG. 2, and FIG. 3A-3B depict plan views of devices 100, 200, and/or 300). As such, device 400 comprises a base structure 402 having a front surface 404 and a back surface 406. A scale 408, which may be similar in one or more aspects to scales 206 and 306, is positioned on the front surface 404 of base structure 402. As previously described scale 408 may be printed, adhered, welded, or joined by any other means known to those of ordinary skill in the art to a surface, such as the front surface 404. The thickness of base structure 402 is represented as thickness 412, and which may be, in one example, 0.25 mm, 0.5 mm, 0.75 mm, or 0.9 mm, and the like.

Figure 4B:
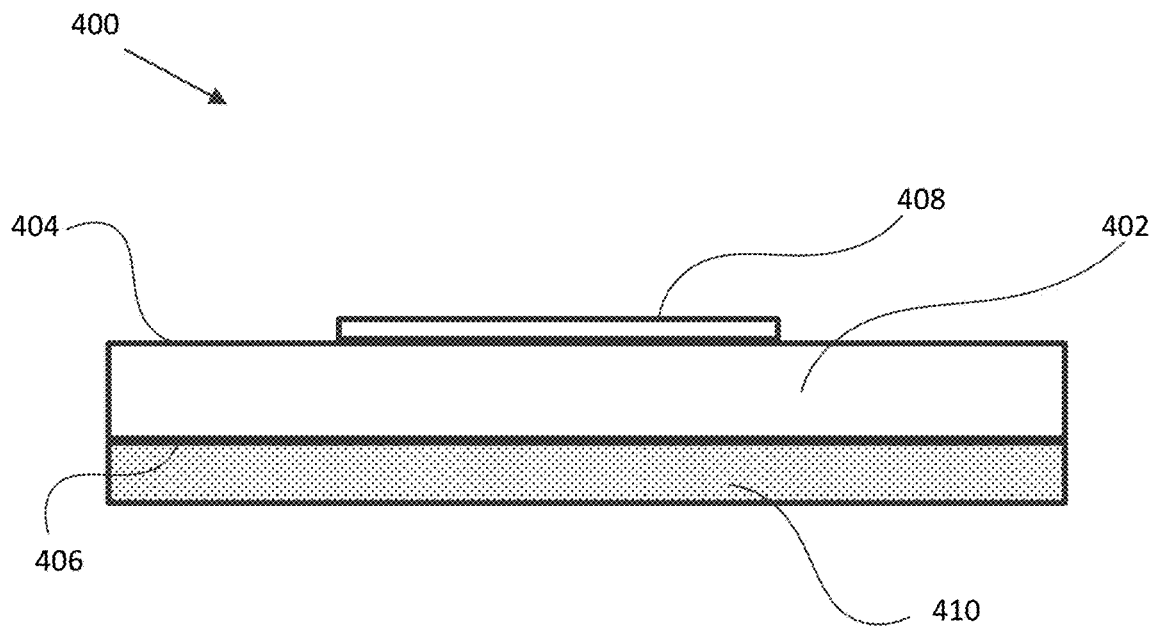

Turning to FIG. 4B, device 400 from FIG. 4A is depicted having an alternative configuration, and including an adhesive layer 410 on the back surface 406 of base structure 402. In one example, adhesive layer 410 may cover the entire surface area of the back surface 406 of base structure 402. In another example, adhesive layer 410 may only partially cover the back surface 406. Specifically, in one example, adhesive layer 410 may cover an outer perimeter area, such as perimeter area 304 from FIG. 3A.

It will be readily apparent to those of skill in the art that adhesive layer 410 may comprise any known adhesive. In one example, adhesive layer 410 may comprise a medical adhesive configured to temporarily and removable bond a structure, such as device 400, to an area of skin of a patient.

Figure 5A:
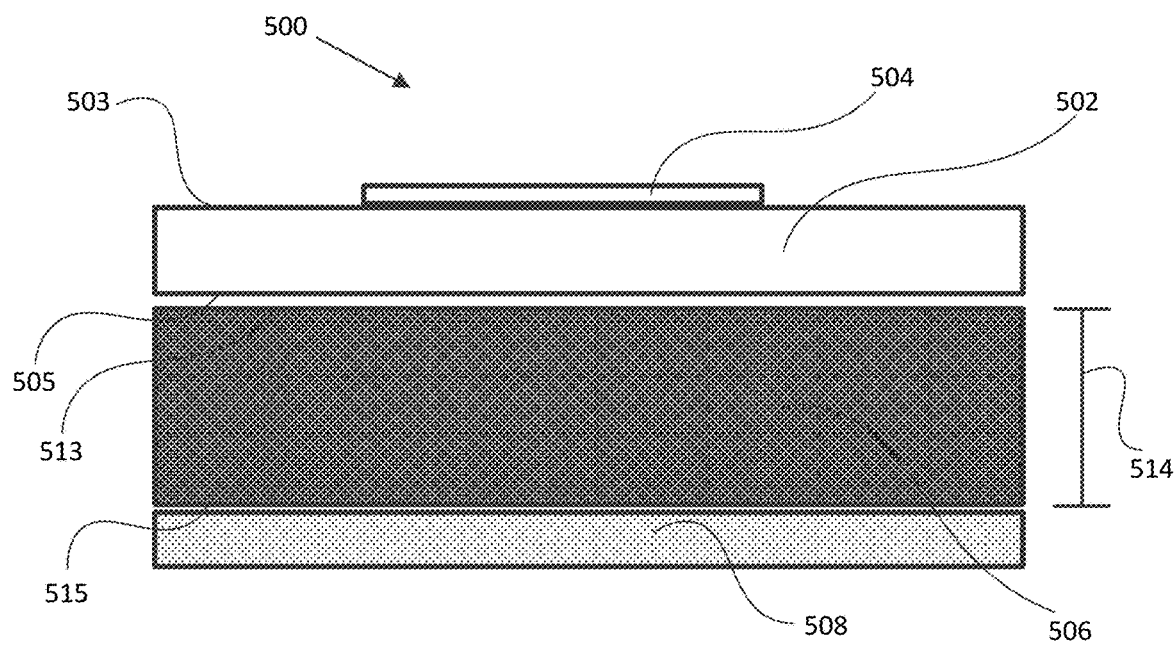
FIG. 5A-5B schematically depict side views of alternative implementations of blood vessel sizing devices having deformable structures.

FIG. 5A schematically depicts device 500. In one example, device 500 may be similar in one or more aspects, to devices 100, 200, 300, and/or 400 previously described. Accordingly, device 500 may comprise a base structure 502, which may be similar to one or more aspects described herein of base structure 102, 202, 302 and/or 402. A scale 504 may be positioned on a front surface 503 of base structure, and a deformable structure 506 may be positioned on a back surface 505 of base structure 502.

As such, a front surface 513 of deformable structure 506 may be adhered to the back surface 505 of base structure 502 by any methodology known to those of ordinary skill in the art, and including, but not limited to, adhesion, molding, fastening, and/or welding, among others. Additionally, an adhesive layer 508, similar to adhesive layer 410, may be positioned on part or all of a back surface 515 of deformable structure 506. It should be understood that deformable structure 506 and adhesive layer 508 may be the same layer. Therefore, discussion of a deformable structure or adhesive layer should be interpreted as a single layer that has both properties.

Deformable structure 506 may comprise a material with physical properties (e.g. hardness) allowing for deformation (compression, and the like) without failure of the material. Accordingly, deformable structure 506 may comprise a sponge-like material which may be a synthetic foam, or any other material with mechanical properties suitable for deformation. Furthermore, in one example, deformable structure 506 may have a thickness 514 of 1 mm, 2 mm, 5 mm, 10 mm, 15 mm, among others.

Figure 5B:
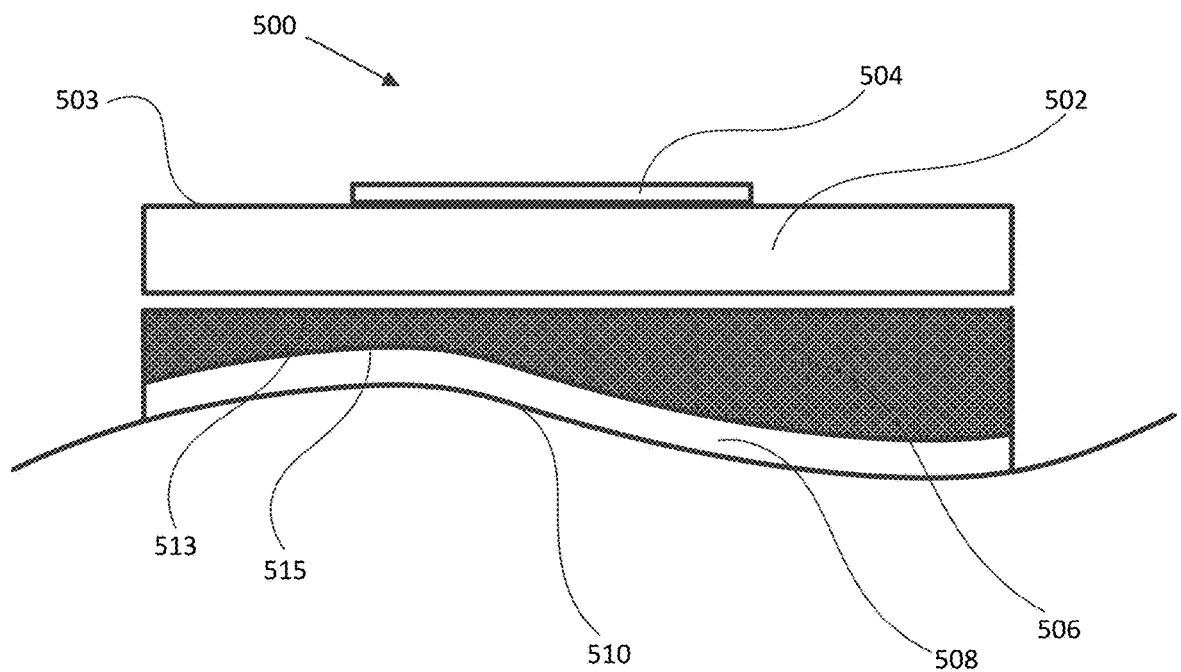

FIG. 5B schematically depicts device 500 adhered to an uneven surface 510. As such, deformable structure 506 is depicted in a compressed state, wherein the back surface 515 of deformable structure 506 conforms to the undulations of uneven surface 510, while the front surface 513 of the deformable structure 506 remains substantially planar. Accordingly, base structure 502 of device 500, in addition to the radiopaque scale 504 thereon, also remain substantially planar while device 500 is adhered to uneven surface 510.

Figure 6A:
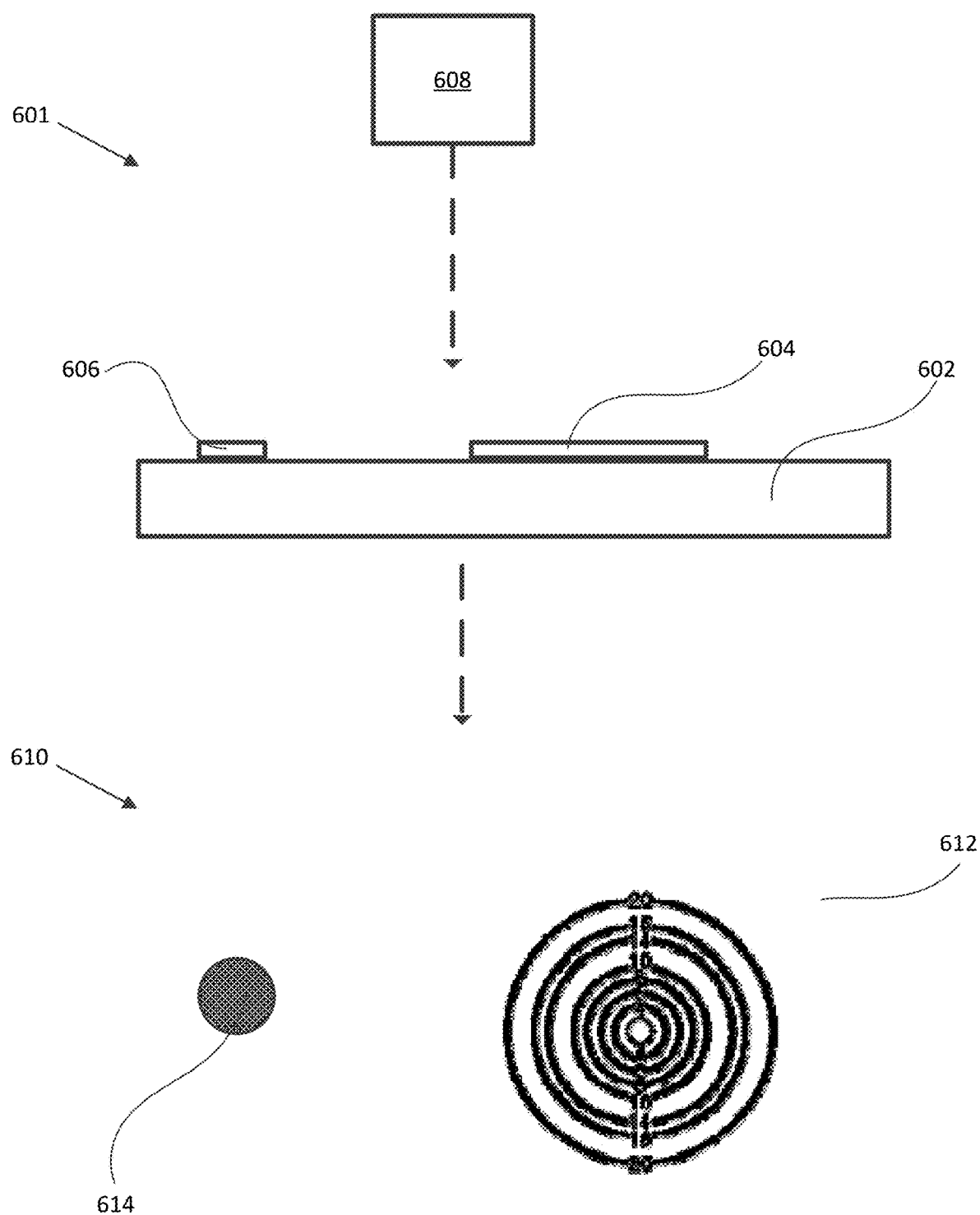
FIG. 6A-6B schematically depict radiographic images produced by blood vessel sizing devices.

FIG. 6A schematically depicts a radiographic image 610 resulting from electromagnetic radiation of a certain wavelength (or range of wavelengths), e.g. x-rays, incident on a device 601 which may be laid over a passageway of a living being, such as a blood vessel of a human. Accordingly, device 601 may be similar in one or more of the aspects described herein to one or more of devices 100, 200, 300, 400, and/or 500. In particular, FIG. 6A schematically depicts a source 608 emitting electromagnetic radiation that is incident upon a base structure 602, a radiopaque scale 604, and a location marker 606 of device 601. In one example, part, or all, of the electromagnetic radiation incident on scale 604 and location marker 606 is absorbed. Yet, other embodiments may have materials that get excited or otherwise react to the imaging process or other process used in conjunction with the imaging process. Accordingly, the radiographic image produced upon detection of the electromagnetic radiation transmitted through base structure 602 includes a radiopaque scale image 612 and a location marker image 614.

Figure 6B:
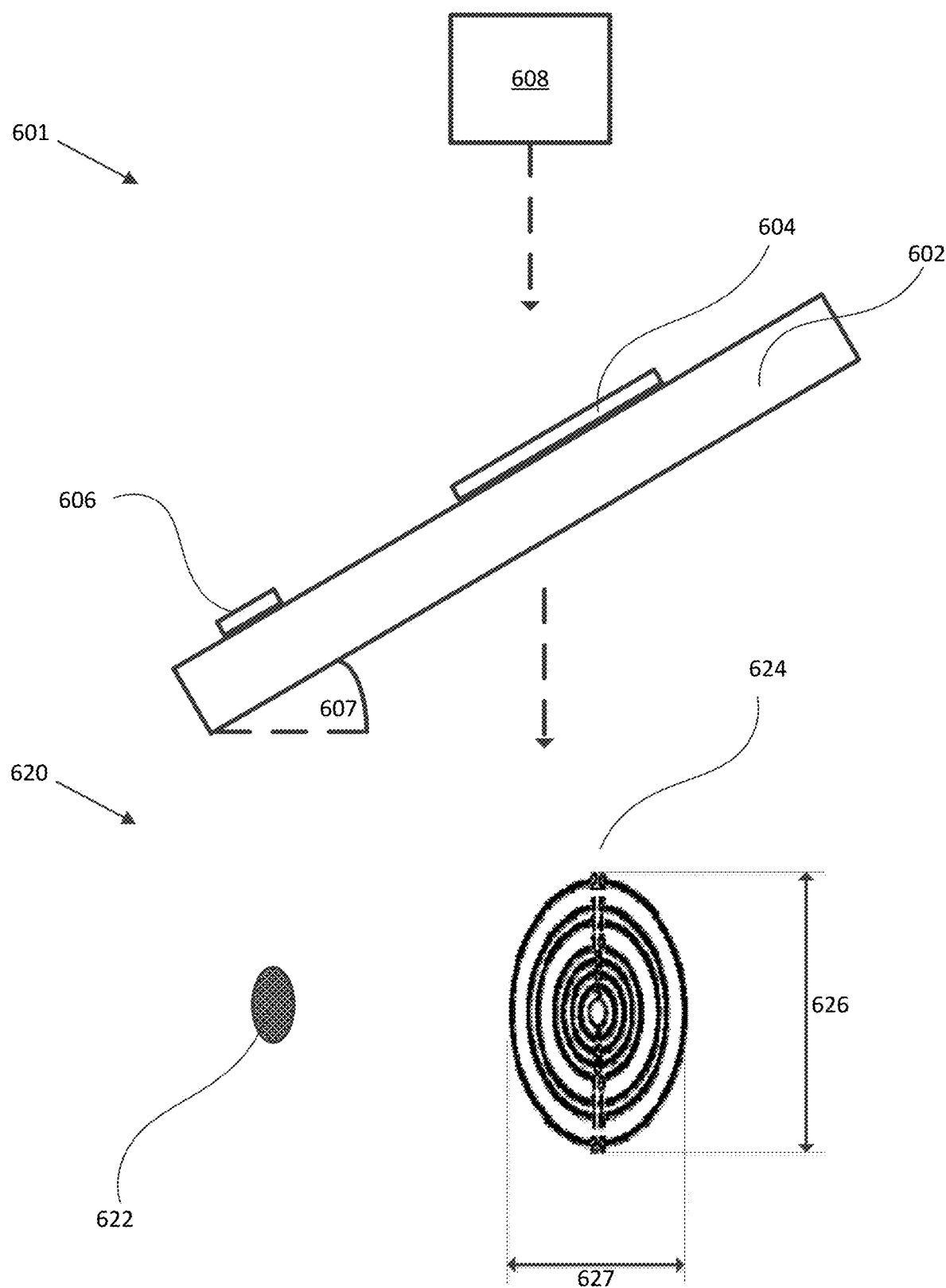

FIG. 6B depicts the same device 601, but angled, at angle 607, with respect to source 608 along a defined plane. Those skilled in the art will appreciate that the device may be angled with respect to the source along multiple planes, however, for sake of understanding aspects of the innovative embodiment, only a single plane is discussed. Because the device 601 is angled with respect to the source, the electromagnetic radiation emitted from source 608 is no longer orthogonal to base structure 602 (electromagnetic radiation now incident upon base structure 602 at an angle of (90°– [angle 607]°)). As such, the radiographic image 620 produced as a result of the angle between the incident radiation and device 601 results in a radiopaque scale marker image 624 and a location marker image 622 having ellipsoidal shapes, as depicted.

The distortion of the radiopaque scale marker image 624 and location marker image 622 may be regarded as an error of parallax, wherein, among others, minor axis 627 of radiopaque scale marker 624 no longer represents a true length. However, due to the concentric-circle design of scale marker 604 (e.g. radiopaque concentric-circle elements 104*a*-104*h* from FIG. 1), the resulting radiopaque scale marker image 624 includes at least one true length. In particular, the true length of concentric-circle elements 104*a*-104*h* is represented in radiopaque scale marker image 624 along the longest axis (major axis) 626 of that ellipsoidal image of radiopaque scale marker 624. As such, a user may determine the longest axis of radiopaque scale marker image 624, and measure one or more true lengths of one or more concentric-circle elements 104*a*-104*h* along said axis 626. In this regard, although there are two axes shown (626 and 627), those skilled in the art will realize that any straight line that passes through the center of a concentric circle can serve as an axis. In this regard, the closest axis to the true axis may be set to the nearest degree, of the circle, or nearest half degree or whole number of degrees. Advantageously, device 601, and in particular, the concentric-circle elements 104*a*-104*h*, thereby allow a user to avoid errors of parallax.

In one example, device 601 may not comprise a rigid structure. In particular, in one example, base structure 602 may bend in one or more directions. For example, base structure 602 may substantially conform to one or more areas of curvature of the human body onto which it is a fixed. As such, due to bending of base structure 602 along one or more axes, a resulting marker image 624 produced by source 608 may be distorted along multiple axes. For example, distortion of marker image 624 may result in a first major axis associated with the depicted 20 mm (which may be other dimensions, such as 30 mm or 3 cm) concentric circle of marker image 624 (e.g. circle 104*h* from FIG. 1), and a second major axis associated with, in one example the 10 mm concentric circle of marker image 624 (e.g. circle 104*d* from FIG. 1), wherein the first and the second major axes are not parallel. As such, in one example, it may be advantageous for a user to determine a concentric circle size, from those concentric circle sizes depicted in marker image 624 (e.g. 2 mm, 4 mm, 6 mm, 8 mm, 10 mm, 14 mm, 16 mm, 20 mm, or 30 cm among others) that most closely matches a dimension of an imaged feature. In this way, a user may identify a first major axis in marker image 624 to be used in association with a first imaged feature, wherein this first major axis is a most accurate axis visible in marker image 624 having a dimension that is close to a dimension to be measured in the first imaged feature. Accordingly, a user may identify a second major axis in marker image 624, due to distortion of marker image 624 as a result of bending of base structure 602 along one or more axes. As such, the second major axis may not be parallel to the first major axis identified. Accordingly, the second major axis may be a most accurate axis visible in marker image 624 having a dimension that is close to a dimension to be measured in a second imaged feature.

Figure 7:
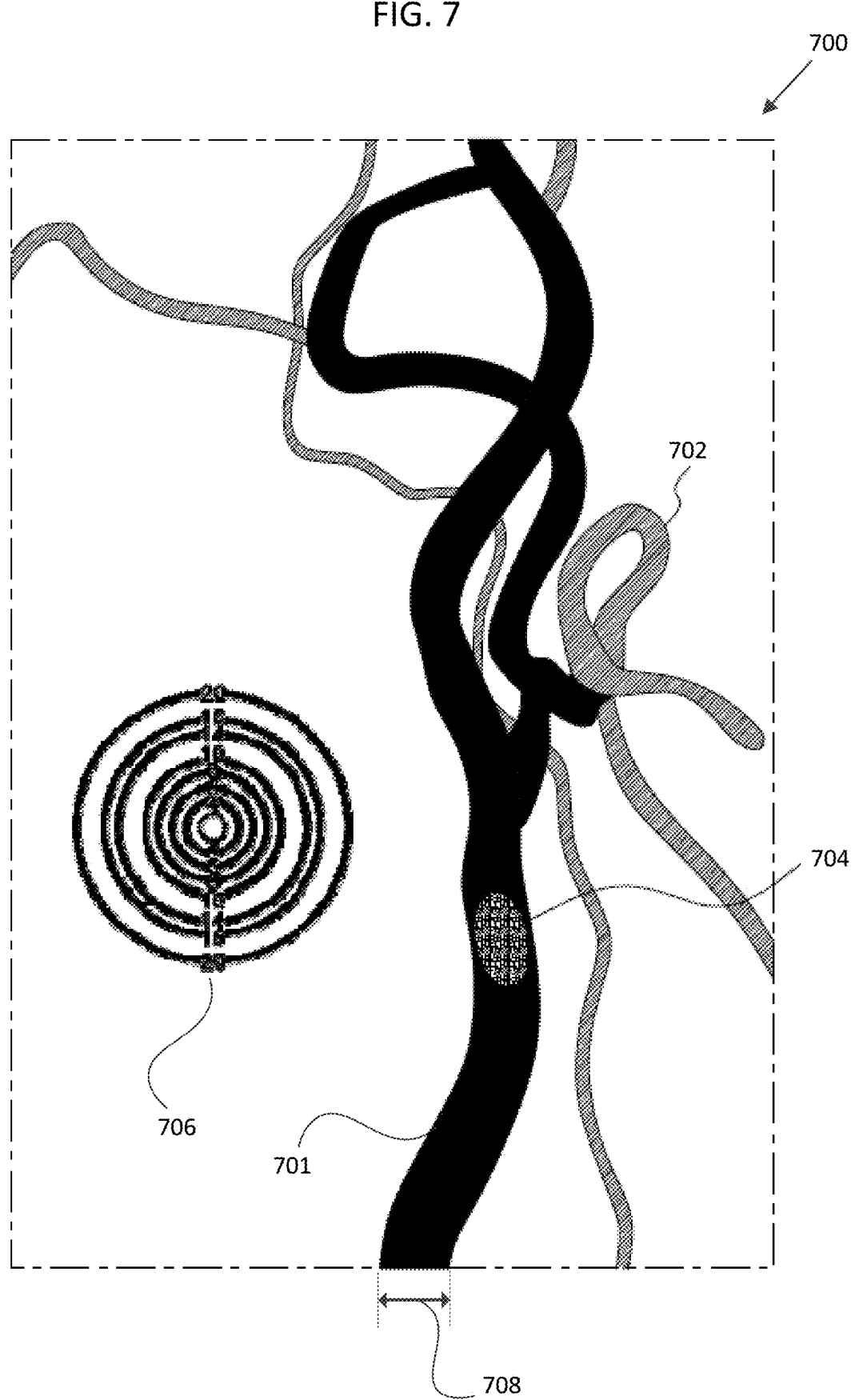
FIG. 7 schematically depicts a radiological image including one or more biological features.

FIG. 7 schematically depicts a radiological image 700, that defined a field of view or target area including one or more biological features (which may include a target object. In particular, the image 700 of FIG. 7 may be an angiogram. Those of ordinary skill in the art will readily understand various methodologies for carrying out an angiogram, which include, among others, use of contrast agents to view blood vessels, and the like. Accordingly, any known technique for angiography or other radiographic imaging may be employed with the systems and methods described herein, and without departing from these disclosures. Furthermore, image 700 may be computer-generated, or may be produced by the detection of electromagnetic radiation (e.g. x-rays) by a film.

FIG. 7 depicts a plurality of blood vessels comprising at least a portion of the carotid artery 701, and one exemplary branching blood vessel is labeled as vessel 702. In one example, it may be desirable to obtain one or more dimensions of biological features from a given radiological image 700. Accordingly, in one example, one or more dimensions of a stenosis 704 may be obtained from radiological image 700. In one implementation, a device, such as device 100, 200, 300, 400, and/or 500 may be positioned on a surface of interest, and within the field of view of a radiological image to be produced. In one specific example, a scale image 706 (which may comprise a plurality of elements and symbols) may be included in a radiological image 700 produced. As such, one or more true dimensions of one or more biological features (e.g. a blood vessel width 708) may be determined using one or more concentric-circle elements of the unknown size (e.g. elements 104*a*-104*h* from FIG. 1) of scale image 706.

Figure 8:
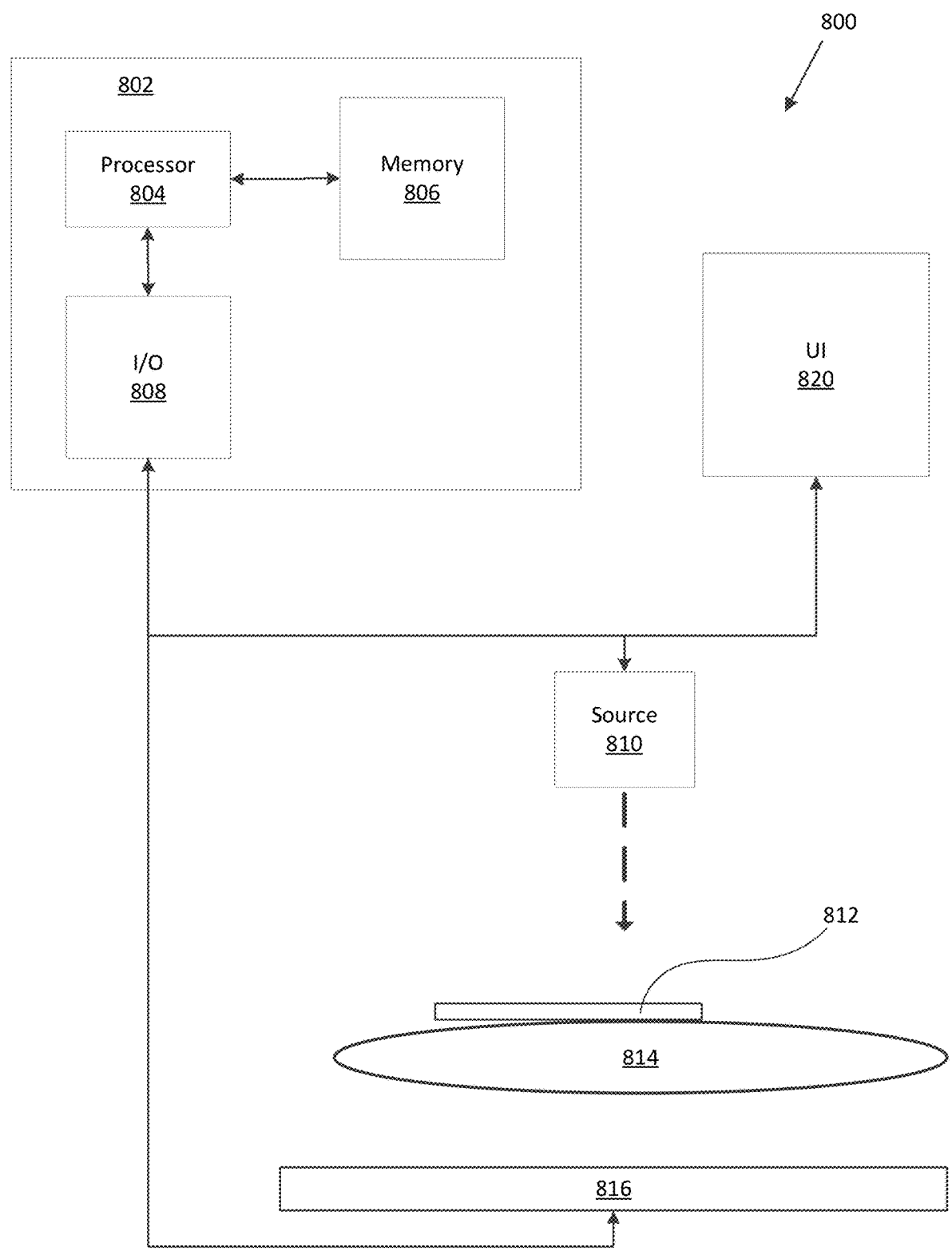
FIG. 8 is a schematic block diagram of an imaging system.

FIG. 8 schematically depicts an imaging system 800. Specifically, system 800 includes a computer 802 having a processor 804, in memory 806, and an interface 808. Computer 802 is further connected to a user interface 820, a source 810, and a detector 816. It will be readily apparent to those of ordinary skill in the art that connections between devices 802, 820, 810, and/or 816 may be wired or wireless, and using any known network type and/or communication protocol. For example, communication between one or more of devices 802, 810, 820, and/or 816 may be through a local area network (LAN), a wide area network (WAN), or the Internet, and using a communication protocol including one or more of the Transmission Control Protocol (TCP), the Internet Protocol (IP), or the User Datagram Protocol (UDP), among many others.

Processor 804 may be a general-purpose central processing unit, or a dedicated and specialized processing chip. Processor 804 may contain a single processing core, or multiple cores acting in parallel, and the like. Memory 806 may be volatile or persistent, and may include one or more of read only memory (ROM), random access memory (RAM), a solid state hard drive (SSD), or memory using optical disc media (CD, DVD, and the like), among others. Interface 808 may comprise those hardware and/or software components for connection of computer 802 to one or more devices 810, 820, and/or 816 across a network. Furthermore, user interface 820 may comprise one or more of a display and/or a control interface for receiving instructions from user. Source 810 may comprise a source of electromagnetic radiation (e.g. x-rays) suitable for radiographic imaging. Accordingly, detector 816 may comprise an electronic detection device sensitive to electromagnetic radiation emitted from source 810, and such that the electromagnetic radiation received by detector 816 may be used to construct a digital image.

Element 814 represents an area of skin of a patient to be imaged using source 810 and detector 816. Positioned on said area of skin of a patient 814 is a blood vessel sizing device 812, wherein the device 812 may be similar to one or more of those devices (100, 200, 300, 400, and/or 500) previously described. Accordingly, one or more features of device 812, such as, for example, a radiopaque scale, such as radiopaque scale 408, may be included in a resulting image constructed by computer 802.

In one example, a user of system 800 may identify a biological feature within a radiological image, wherein said image may be a real-time digital image produced by computer 802 from data received from detector 816. For example, a user may identify a one or more passageways (blood vessels) and/or one or more objects within passage ways (blood clots), among others. In one example, it may be desirable for a user to determine a true dimension of one or more biological features present in an image produced by system 800. Accordingly, a user may input one or more instructions, via interface 820, identifying one or more biological features of interest within an image produced by system 800, and visible to a user at user interface 820. Subsequently, one or more identified features of interest may be compared to an image produced by blood vessel sizing device 812, wherein said image may be similar to a scale, such as scale 612 and/or scale 624, among others. As such, one or more known sizes/dimensions of said scales 612 and/or 624 may be compared to the one or more identified features of interest, and a true dimension may be determined. Furthermore, it will be apparent to those of ordinary skill that blood vessel size or device 812 is agnostic to the type of imaging equipment used, in addition to the magnification and/or specific image manipulation processes applied to the data detected by detector 816.

In one example, a user may manually compare a length property of a biological feature visible within an image produced by system 800 to one or more known dimensions of a radiopaque scale present within said image. For example, a user may measure a width of a blood vessel, as shown in an image produced by system 800, using a calipers. However, due to the magnification/scaling and/or other image manipulation steps carried out on the data received from detector 816, this length measured by the calipers may not be a true dimension of the width of the blood vessel. Accordingly, the user may compare the length measured by the calipers to one or more concentric-circle elements (e.g. elements 104a-104h from FIG. 1) visible within a radiopaque scale (e.g. radiopaque scale 612 and/or 624), and wherein the radiopaque scale is visible within the same radiological image as the blood vessel of interest (e.g the visible radiopaque scale 612 and/or 624 will have been subject the same scaling and/or other image manipulation processes such that a direct comparison between the length measured with the calipers, and one or more lengths from the radiopaque scale is still possible). In doing so, the user may compare the measured length from the calipers to the major axis (e.g. as discussed in relation to FIG. 6B) of the radiopaque scale, and by comparison to one or more of the known dimensions of the concentric-circle elements, determine a true dimension of the blood vessel width. Furthermore, it will be readily apparent to those of skill that any mechanical measurement device may be utilized for measuring a length property of a biological feature. For example, a user may utilize a ruler, measuring tape, or calipers, among many others.

In another example, one or more true dimensions of an identified biological feature may be determined by an automated process. One example of such an automated process is described in relation to FIG. 9.

Figure 9:
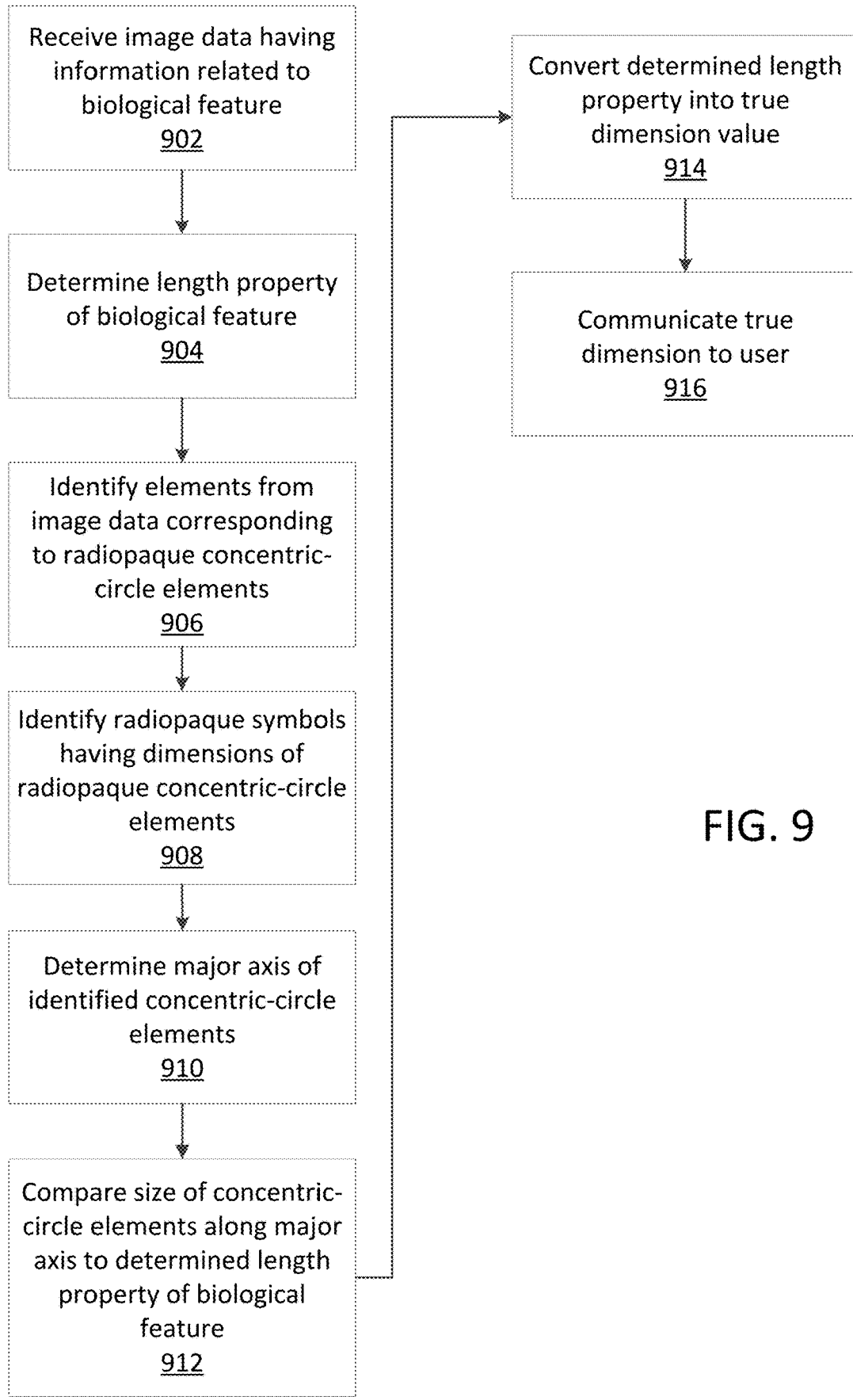
FIG. 9 is a flowchart diagram of one or more processes for automatically determining a true dimension of a future captured in a radiological image.

FIG. 9 is a flowchart that may be implemented in the automatic determination of a true dimension of a feature captured in a radiological image (e.g., radiograph/x-ray). In one example, the description in FIG. 9 may be used in conjunction with imaging system 800 from FIG. 8. Image data may be received from a detector, such as detector 816 (e.g., block 902). In one example, this image data may include information related to one or more biological features (tissues, organs, blood vessels, blood clots, and the like). A dimensional property (e.g., a length property) of the one or more biological features of interest within the received image data may be obtained (e.g., block 904, which may follow block 902).

In an example embodiment, block 904 may represent one or more processes to determine a length of one or more features within a radiological image using an arbitrary length metric (e.g. a number of screen pixels, and the like). In this way, due to one or more scaling and/or other image manipulation processes carried out on the image data used to create the radiological image, a true dimension of the one or more features is not readily known.

One or more elements from image data that correspond to concentric-circle elements, such as those elements 104a-104h from FIG. 1, may be identified (e.g., block 906). Block 906 may occur in the absence of block 904. Those of ordinary skill in the art will readily understand that any computer image recognition processes may be utilized with the one or more processes of block 906, and without departing from the scope of this disclosure.

Symbols, such as for example, 106a-106g and 107a-107g, may be identified from the image data. This may occur before, during, after and/or in absence of blocks 904/906. In accordance with further embodiments, a major axis of one or more identified concentric-circle elements may be determined, such as at block 910. In this way, and as described in relation to FIG. 6B, a longest axis of a radiopaque scale marker image, such as radiopaque scale marker image 624 from FIG. 6B, may be used to read known lengths of one or more concentric-circle elements 104a-104h without an error of parallax (and/or with a statistically significant reduction in an error of parallax.

A dimensional property (e.g., the length property) of a biological feature may be compared to one or more dimensions (e.g., lengths) of concentric-circle elements along the determined major axis of a radiopaque scale marker image, such as radiopaque scale marker image 624. Upon comparison of the determined length property of the biological feature to the corresponding concentric-circle elements of the same length (or interpolating/extrapolating from one or more known dimensions of concentric-circle elements), a true dimension value may be determined. As such, the determined dimensional property (e.g., the length) of the biological feature may be converted into a true dimension value (e.g., block 914).

A true dimension value may be communicated to a user, such as via user interface 820 from FIG. 8, which may occur at example block 916.

Figure 10B:
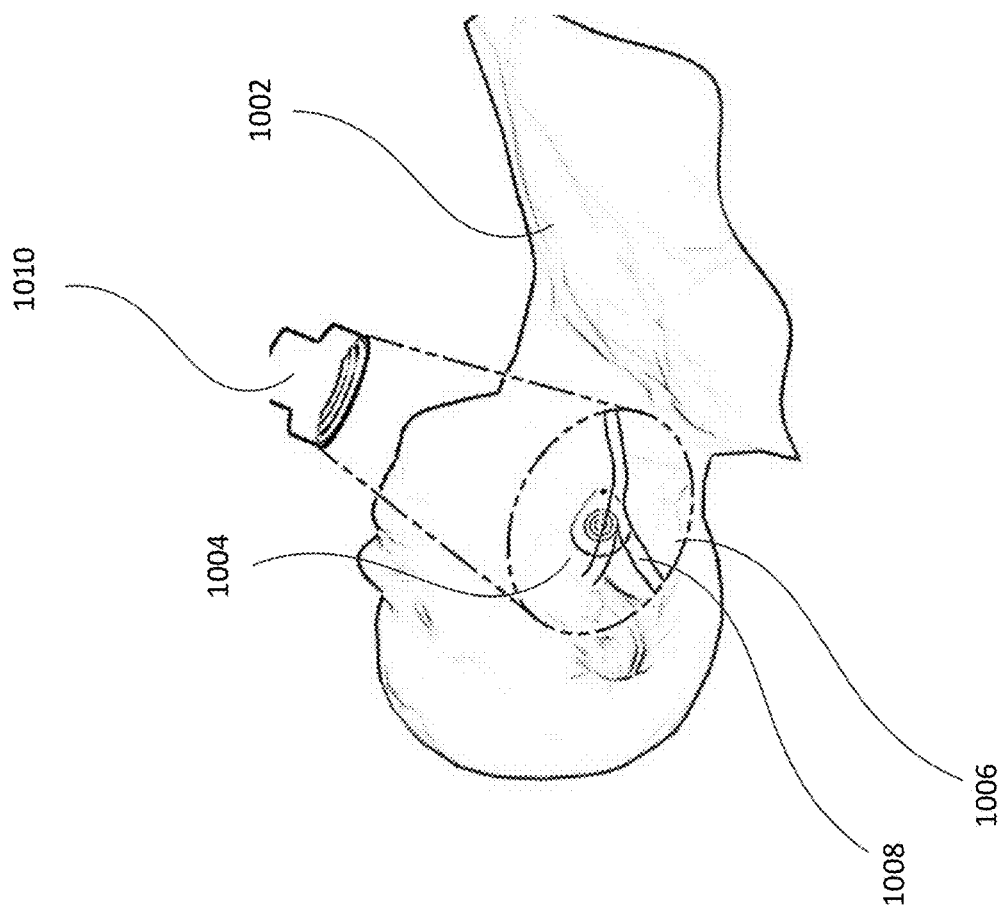
FIG. 10A-10B schematically depict a blood vessel sizing device being used on a human patient.
Figure 10A:
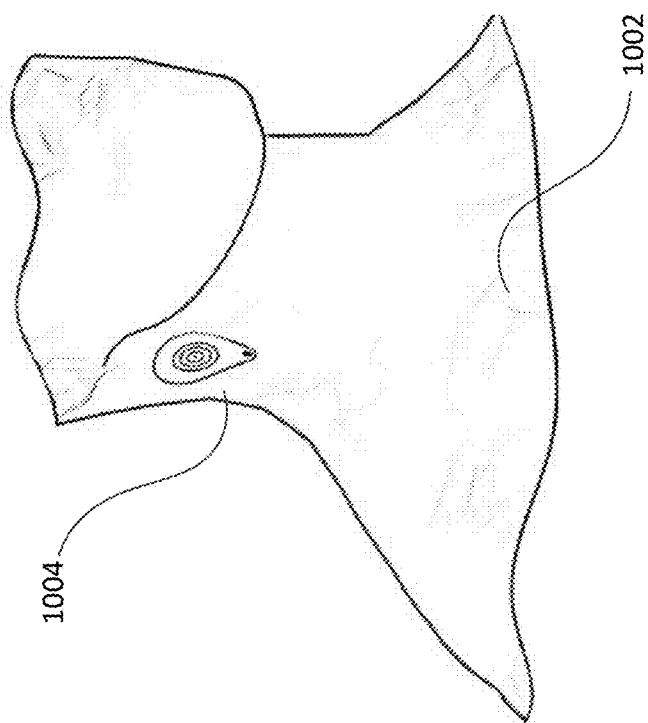

FIG. 10A schematically depicts an example implementation of device 1004 being used. In particular, FIG. 10A schematically depicts device 1004 positioned on a neck area of a human patient 1002. Accordingly, in one implementation, device 1004 may be similar to device 100, 200, 300, or 400, and the like. Following from FIG. 10A, FIG. 10 B schematically depicts patient 1002 being imaged using imaging device 1010. As will be apparent to those of ordinary skill in the art from the foregoing disclosures described herein, imaging device 1010 may be, among others, part of an x-ray device for performing an angiogram. In other implementations, device 1010 may be a part of an MRI device, a CT device, a myelogram device, a thermograph device, an MRN device, an ultrasound device, and/or combinations thereof, among others.

Accordingly, as schematically depicted in FIG. 10B, imaging device 1010 may image a region 1006 that includes both device 1004 and, in one example, blood vessel 1008. In one specific example, blood vessel 1008 may be a carotid artery, among others.

Figure 11A:
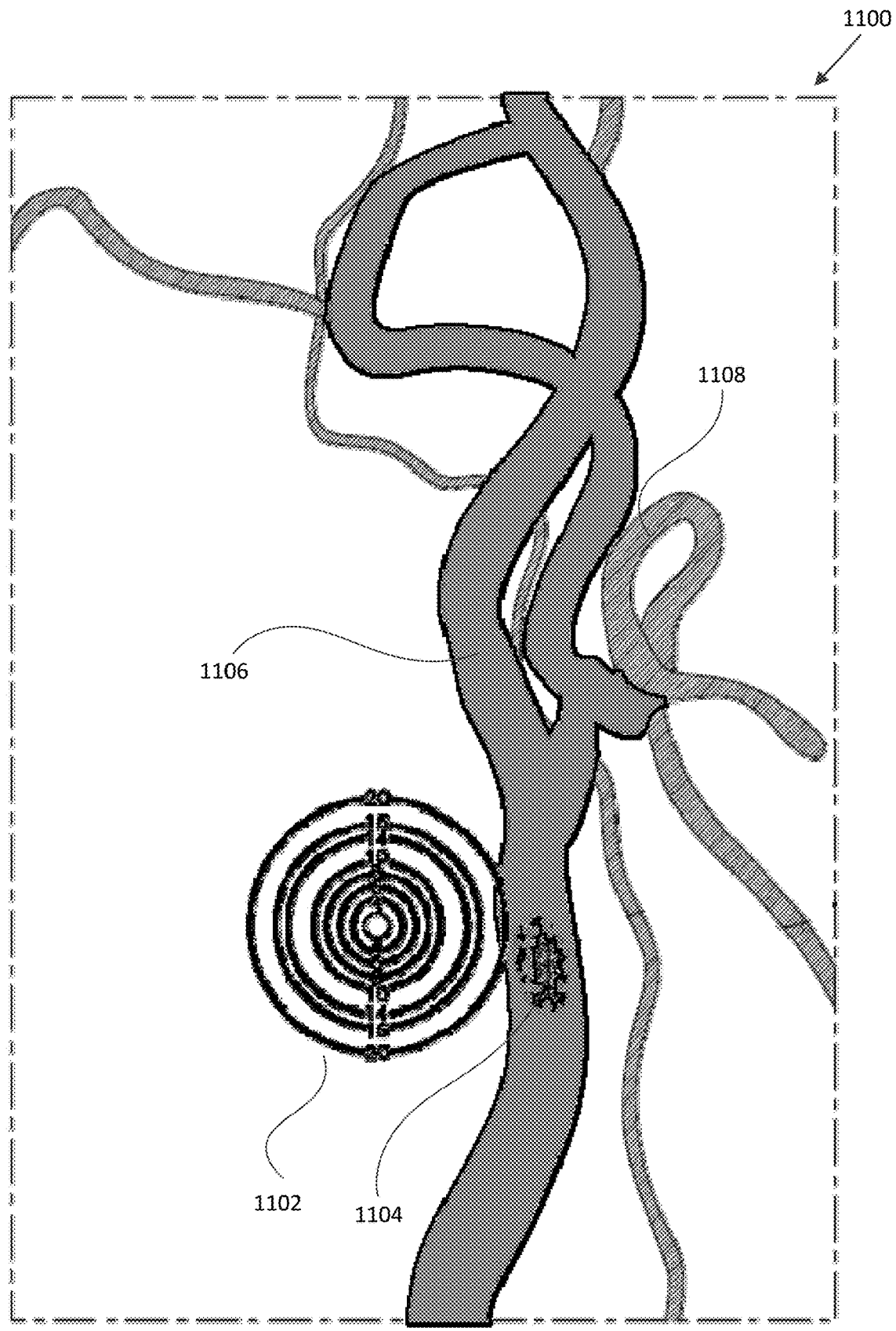
FIGS. 11A-11D schematically depict various implementations of a device that may be utilized for locating an area of interest within a radiological image.

FIGS. 11A-11D schematically depict various implementations of a device that may be utilized for locating an area of interest within a radiological image. In certain embodiments disclosed herein, the device may be used to locate or estimate the location of a feature or area of interest of: (1) a first image of a first area, wherein a first feature is captured under a first image criteria; and (2) a second image that comprises at least the same first area, wherein the same feature is present but not captured or captured to a less degree, under a second image criteria, Non-limiting examples are discussed in relation to FIGS. 11A-11D. In one example, FIG. 11A depicts a radiological image 1100 that includes a scale image 1102, which may be similar to scale image 706, and generated as a result of one or more imaging processes of a device, such as device 100, and the like. Additionally, FIG. 11A depicts a schematic view of a blood vessel 1106 having a feature of interest 1104, which may be, in one example, a stenosis, and the like. Furthermore, FIG. 11A depicts a branching vessel 1108. In one example, vessel 1106 and feature 1104 may be visible within an image (e.g., radiological image) 1100 through use of a contrast agent. In this regard, FIG. 11A may represent a first image of a first area, wherein the feature 1104 may be a first feature that is captured under the specific capturing conditions, such as using a radiograph and contrast agent (or specific type/dosage of agent).

Figure 11B:
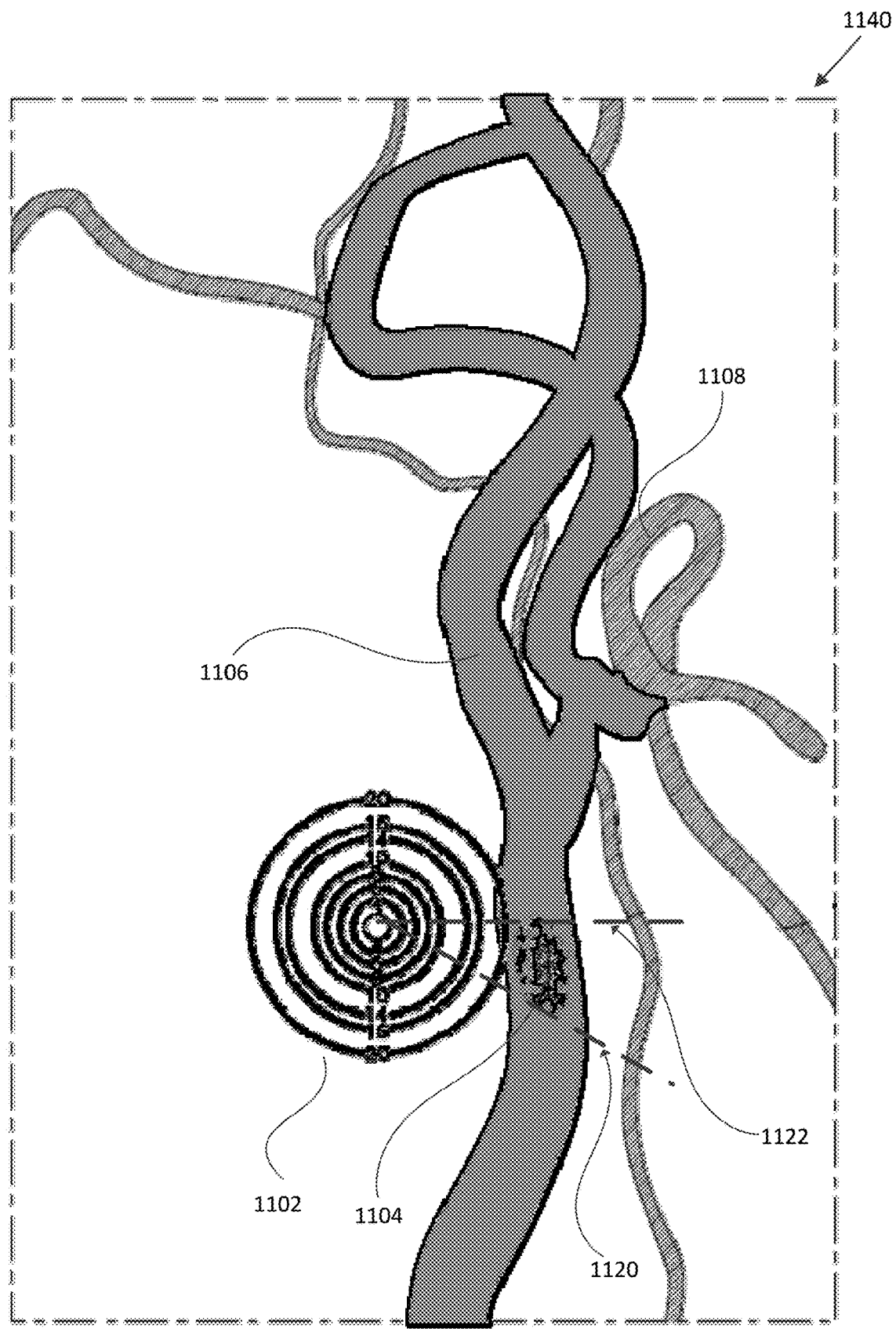

FIG. 11B schematically depicts a radiological image 1140 that is similar to image 1100 from FIG. 11A. In particular, FIG. 11B schematically depicts scale image 1102 being utilized to locate a feature of interest 1104. Specifically, a position of scale image 1102 may be noted relative to feature 1104. Accordingly, those lines 1120 and 1122 may represent imaginary lines, or visible lines depicted on an electronic interface (computer screen) or other representation of image 1140 (e.g. a printed copy of image 1140, and the like) that may be traced out from the center of scale image 1102, and delimiting of the ends of feature 1104 within vessel 1106. For example, a user (a clinician or otherwise) viewing image 1140 may note that a "top" end of feature 1104 corresponds to a "3 o'clock position" at an outer concentric-circle element (that largest 20 mm circular element depicted, which may be larger or smaller, including, for example, 30 mm or 3 cm), and delimited by line 1122. Similarly, the user may note that a "bottom" end of feature 1104 corresponds approximately to a "4 o'clock position" at the outer concentric circle of scale image 1102, and delimited by line 1120. As such, while vessel 1106 and feature 1104 are visible in image 1140 through use of a contrast agent, noting a position of feature 1104 relative to scale image 1102 may allow said feature 1104 to be located without using further contrast agent in subsequent images having a same field of view.

In furtherance of this example, those of ordinary skill in the art will readily understand various contrast agents, otherwise referred to as radiocontrast agents, or contrast media, among others, may be used to improve visibility of one or more blood vessels, and associated features, when imaged using x-ray-based imaging techniques. Accordingly, in one example, a contrast agent may be utilized in image 1100 to view vessel 1106, and may include an iodinated (iodine-based) contrast agent, among others. As such, those of ordinary skill in the art will understand that while contrast agents are generally considered safe for use during in vivo imaging, there exist various side effects that may be associated with the use of contrast agents. For example, contrast agents may have a detrimental impact upon kidney function, or may, in some instances, lead to higher rates of blood clotting, among others. As such, it may be desirable for an imaging process to reduce an amount of contrast agent utilized to, in one example, image a vessel for positioning of a stent, among others. Thus, a second image (which may be a subsequent frame in a live video capture) may be the same area and feature (e.g., feature 1104), however, blood flow has moved the contrast agent, and as such, feature 1104 may be less visible or not visible.

Figure 11C:
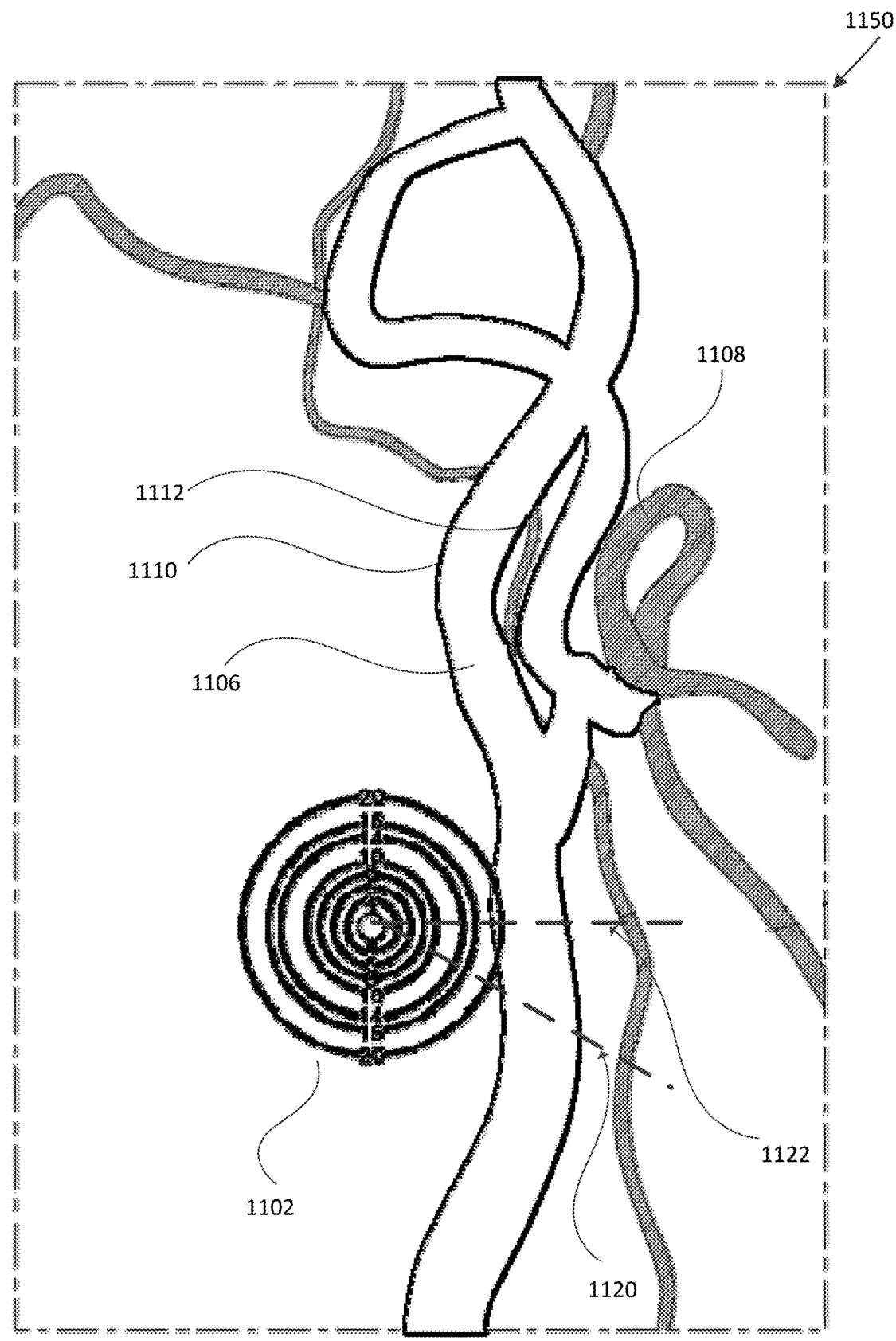
Figure 11D:
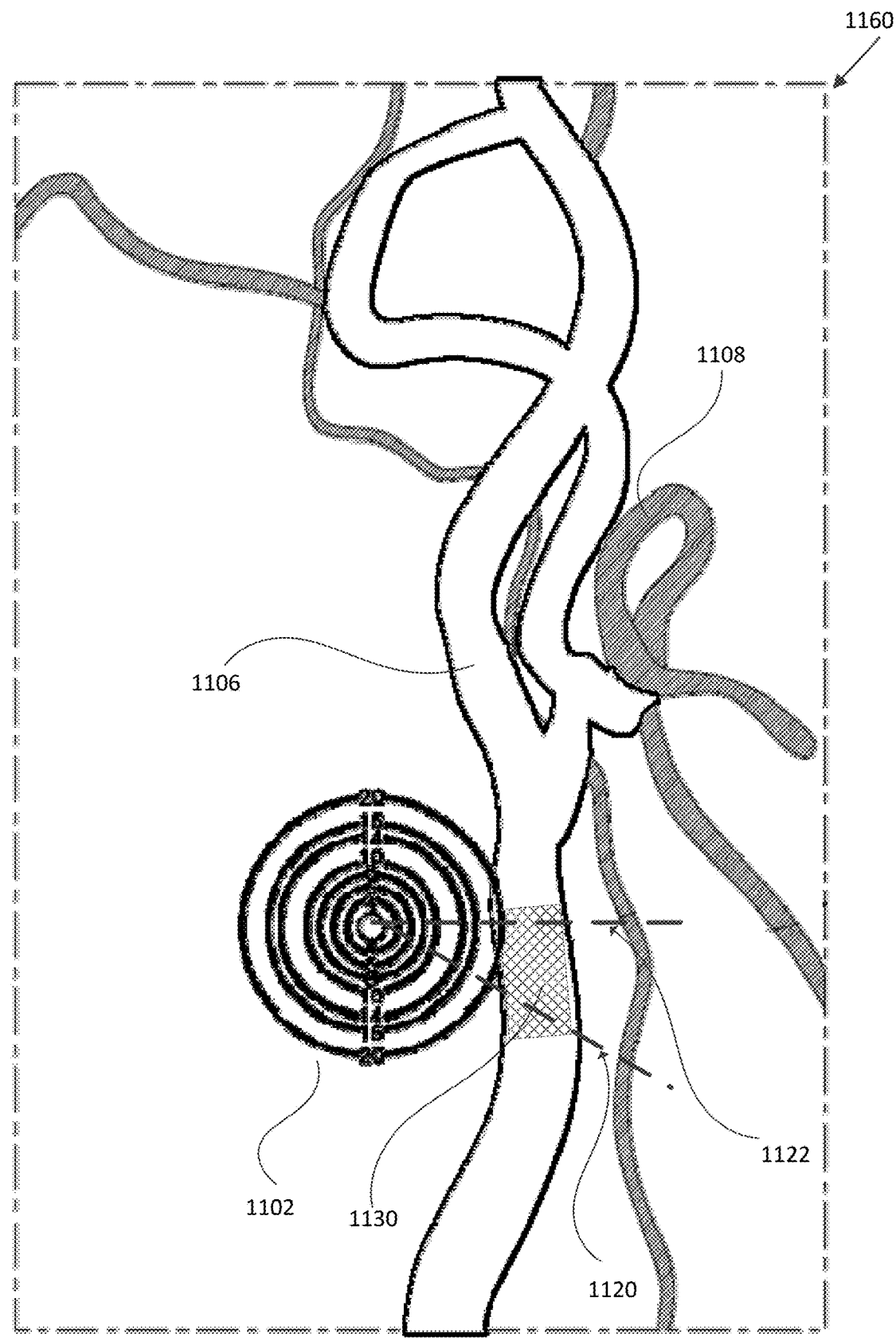

FIG. 11C schematically depicts scale image 1102 being utilized to locate a feature within a vessel 1106 without using contrast agent. As such, respective to FIG. 11A, FIG. 11C may be considered a second image that comprises at least the same first area, wherein the same feature is present but not captured or captured to a less degree, under a second image criteria (e.g., no or less contrast agent). In one embodiment, at least a portion of the vessel itself may be the feature that is less visible or not visible in the second image (or any image that is not the first image). In particular, an outline of vessel 1106 is depicted in FIG. 11C, having a first side wall 1110, and a second sidewall 1112. However, sidewalls 1110 and 1112 outlining vessel 1106 are included for clarity within radiological image 1150. As such, sidewalls 1110 and 1112 represent one or more lengths of blood vessel 1106 that were previously visible within the radiological image 1140 from FIG. 11B through use of a contrast agent, but which may no longer be visible, or may have diminished visibility, within radiological image 1150 due to an absence of a contrast agent. As such, it may be assumed that sidewalls 1110 and/or 1112 of the vessel 1106 are not clearly visible within radiological image 1150 in accordance to one embodiment. However, having noted the position of feature 1104 (which also may not be visible or is of reduced visibility relative to scale image 1102 from FIG. 11B), lines 1120 and/or 1122 may be utilized to locate, approximately, feature 1104 (from FIG. 11B) within image 1150. As such, lines 1120 and/or 1122 may be utilized to position, in one example, a stent, at the feature of interest 1104 from FIG. 11B, and without using, or using a reduced amount of a contrast agent. Turning to FIG. 11D, stent 1130 may be positioned in image 1160 relative to scale image 1102, and utilizing that relative positioning noted using lines 1120 and/or 1122, and the like. Specifically, stent 1130 may be moved into an area of vessel 1106 (vessel 1106 may not be clearly visible within image 1160 due to absence of contrast agent, and the like) by positioning relative to lines 1120 and 1122.

Those of ordinary skill in the art will understand that images 1100, 1140, 1150, and/or 1160 may be still images, or may be "live" images that are periodically updated. In one example, one or more of said images may be updated as a frame rate of six frames per second, however those of ordinary skill in the art will understand that any update/refresh rate may be utilized without departing from the scope of these disclosures. Additionally, those of ordinary skill in the art will understand that's images 1100, 1140, 1150, and/or 1116 may be generated using any appropriate imaging technology including, among others, computed tomography and/or radiography, among many others.

Aspects of the Present Disclosure

Aspects of the subject matter described herein may be useful alone or in combination with one or more other aspect described herein. Without limiting the foregoing description, in a first aspect of the present disclosure, a blood vessel sizing device includes a marker configured for placement on the skin of a patient, the marker defines a substantially circular shape and includes a plurality of radiopaque substantially concentric circles.

In accordance with a second aspect of the present disclosure, which can be used in combination with the first aspect or any one of aspects two to twenty, the blood vessel sizing device includes an adhesive for adhering the device to the skin of the patient.

In accordance with a third aspect of the present disclosure, which can be used in combination with any one or more of the preceding aspects, the blood vessel sizing device includes a plurality of different radiopaque symbols, wherein each of the plurality of different radiopaque symbols represents a diameter of one of the plurality of concentric-circle elements.

In accordance with a fourth aspect of the present disclosure, which can be used in combination with any one or more of the preceding aspects, each of the radiopaque symbols is a geometric shape.

In accordance with a fifth aspect of the present disclosure, which can be used in combination with any one or more of the preceding aspects, each of the radiopaque symbols are numbers.

In accordance with a sixth aspect of the present disclosure, which can be used in combination with any one or more of the preceding aspects, each of the plurality of radiopaque concentric-circle elements has a diameter, the diameters ranging from 2 mm to 12 mm.

In accordance with a seventh aspect of the present disclosure, which can be used in combination with any one or more of the preceding aspects, each of the plurality of radiopaque concentric-circle elements includes at least three radiopaque substantially concentric circles.

In accordance with an eighth aspect of the present disclosure, which can be used in combination any one or more of the preceding aspects, the at least three radiopaque substantially concentric circles have diameters of about 6 mm, 8 mm, and 10 mm.

In accordance with a ninth aspect of the present disclosure, which can be used in combination with any one or more of the preceding aspects, the plurality of radiopaque concentric-circle elements includes at least four radiopaque substantially concentric circles.

In accordance with a tenth aspect of the present disclosure, which can be used in combination with the fifth aspect, the at least four substantially concentric circles have diameters of about 4 mm, 6 mm, 8 mm, and 10 mm.

In accordance with an eleventh aspect of the present disclosure, which can be used in combination with the fifth aspect, the at least four substantially concentric circles have diameters of about 14 mm, 16 mm, 18 mm, and 20 mm.

In accordance with a twelfth aspect of the present disclosure, which can be used in combination with the twelfth aspect, the plurality of radiopaque symbols are at least one of (i) geometric shapes, and (ii) numbers.

In accordance with a thirteenth aspect of the present disclosure, which can be used in combination with any one or more of the preceding aspects, the diameters of the plurality of substantially concentric circles range from about 2 mm to about 20 mm.

In accordance with a fourteenth aspect of the present disclosure, which can be used in combination with any one or more of the preceding aspects, a blood vessel sizing method includes placing a device having a plurality of radiopaque concentric-circle elements on the skin of a patient, imaging the blood vessel and the device, and comparing the image of the blood vessel to the image of at least one of the plurality of radiopaque concentric circle elements to determine a size of the blood vessel.

In accordance with a fifteenth aspect of the present disclosure, which can be used in combination with the fourteenth aspect, imaging the blood vessel and the marker includes using an angiogram.

In accordance with a sixteenth aspect of the present disclosure, which can be used in combination any one or more of the preceding aspects, comparing the imaged blood vessel to the imaged plurality of concentric circles to determine the size of the blood vessel includes measuring the imaged blood vessel and comparing the measured blood vessel to the imaged diameters of the plurality of radiopaque substantially concentric circles.

In accordance with an seventeenth aspect of the present disclosure, which can be used in combination any one or more of the preceding aspects, measuring the diameter of the imaged blood vessel includes using a mechanical instrument.

In accordance with a eighteenth aspect of the present disclosure, which can be used in combination any one or more of the preceding aspects, the marker includes a plurality of different radiopaque symbols, wherein each of the plurality of different radiopaque symbols represents a diameter of one of the plurality of concentric-circle elements.

In accordance with a nineteenth aspect of the present disclosure, which can be used in combination any one or more of the preceding aspects, comparing the imaged blood vessel to the image of at least one of the plurality of concentric circles to determine the size of the blood vessel includes measuring the imaged blood vessel and comparing the measured blood vessel to the imaged diameters of the plurality of radiopaque concentric-circle elements and reading the symbols.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

I claim:

1. A method comprising:
   receiving data corresponding to a biological feature present in radiological image data;
   determining a dimensional property of the feature;
      identifying one or more elements from the image data corresponding to a plurality of radiopaque, concentric-circles of a sizing device positioned on an area of skin of a patient;
      identifying a dimensional property for each of the identified one or more elements;
      determining a longest axis of the identified one or more elements;
      comparing the determined dimensional property of the feature to the identified one or more elements, along the determined longest axis; and
      converting the determined dimensional property of the feature into a true dimension value for communication to a user.

2. The method of claim 1, further comprising:
   identifying one or more radiopaque symbols corresponding to the one or more dimensional properties of the identified one or more elements.

3. The method of claim 1, further comprising:
   after receiving data corresponding to the biological feature present in the radiological image data, removing a non-adhesive tab structure projecting from a side of a base structure of the sizing device, for facilitating facile removal of the sizing device from the area of skin of the patient.

4. The method of claim 1, further comprising:
   uniquely identifying the sizing device by using a radiopaque unique identifier on the sizing device.

5. The method of claim 4, wherein uniquely identifying the sizing device comprises reading a machine-readable barcode.

6. The method of claim 1, further comprising:
   locating the sizing device in a radiographic image by utilizing a radiopaque location marker having a surface area of between 18 and 22 square millimeters.

7. The method of claim 1, wherein the sizing device comprises a polymeric material.

8. The method of claim 1, wherein the sizing device comprises a base structure that is substantially transparent to light with a wavelength in the visible spectrum.

9. The method of claim 1, wherein the receiving data corresponding to the biological feature comprises receiving radiological image data of a blood vessel.

10. The method of claim 9, wherein the identifying the dimensional property for each of the identified one or more elements comprises measuring imaged diameters of the plurality of radiopaque concentric-circles.

11. A sizing device, comprising:
   a planar base structure having a front surface and a back surface, wherein the base structure is:
   configured to be placed on a user's skin to capture a target area of a patient having a passageway; and
   substantially transparent to light with a wavelength in the visible spectrum;
   a plurality of radiopaque concentric-circle elements positioned on the front surface of the base structure; and
   a plurality of radiopaque symbols positioned on the base structure, wherein each symbol of the plurality of symbols represents a dimensional property of at least one of the concentric-circle radiopaque elements, wherein the concentric-circle radiopaque elements are configured to be detected by radiological imaging equipment to enable a determination of a size of the passageway without errors of parallax.

12. The sizing device of claim 11, further comprising:
   a deformable structure having a front surface and a back surface, the front surface of the deformable structure adhered to the back surface of the base structure.

13. The sizing device of claim 12, further comprising:
   a window, formed by an adhesion of the front surface of the deformable structure to a perimeter area of the back surface of the base structure.

14. The sizing device of claim 12, wherein the front surface of the deformable structure completely covers the back surface of the base structure.

15. The sizing device of claim 12, wherein the deformable structure comprises a sponge-like material.

16. The sizing device of claim 11, wherein the base structure comprises a polymeric material.

17. The sizing device of claim 11, further comprising:
   a non-adhesive tab structure projecting from a side of the base structure, for facilitating facile removal of the sizing device from an area of skin of the patient.

18. The sizing device of claim 11, wherein the sizing device is uniquely identified by a radiopaque unique identifier on the base structure.

19. The sizing device of claim 18, wherein the radiopaque unique identifier comprises a machine-readable barcode.

20. The sizing device of claim 11, further comprising:
   a radiopaque location marker on the front surface of the base structure that is distinct from the radiopaque concentric-circle elements and the symbols configured to aid in locating the sizing device in a captured radiological image.

* * * * *